US011748800B1

(12) United States Patent
Yuan et al.

(10) Patent No.: US 11,748,800 B1
(45) Date of Patent: Sep. 5, 2023

(54) GENERATING SKIN CARE RECOMMENDATIONS FOR A USER BASED ON SKIN PRODUCT ATTRIBUTES AND USER LOCATION AND DEMOGRAPHIC DATA

(71) Applicant: Life Spectacular, Inc., San Francisco, CA (US)

(72) Inventors: Zaoshi Amy Yuan, San Francisco, CA (US); Ming S. Zhao, San Francisco, CA (US)

(73) Assignee: LIFE SPECTACULAR, INC., San Francisco, CA (US)

( * ) Notice: Subject to any disclaimer, the term of this patent is extended or adjusted under 35 U.S.C. 154(b) by 0 days.

(21) Appl. No.: 17/016,342

(22) Filed: Sep. 9, 2020

Related U.S. Application Data

(60) Provisional application No. 62/899,127, filed on Sep. 11, 2019.

(51) Int. Cl.
| | |
|---|---|
| *G16H 20/00* | (2018.01) |
| *G16H 50/70* | (2018.01) |
| *G06Q 30/0601* | (2023.01) |
| *G06N 20/00* | (2019.01) |
| *G06Q 30/0282* | (2023.01) |
| *A61K 8/00* | (2006.01) |
| *A61Q 19/00* | (2006.01) |
| *A61Q 19/08* | (2006.01) |
| *A61Q 19/10* | (2006.01) |
| *G01N 33/68* | (2006.01) |
| *A61N 5/06* | (2006.01) |

(Continued)

(52) U.S. Cl.
CPC ......... *G06Q 30/0631* (2013.01); *A61B 5/441* (2013.01); *A61K 8/00* (2013.01); *A61N 5/0616* (2013.01); *A61Q 19/005* (2013.01); *A61Q 19/007* (2013.01); *A61Q 19/008* (2013.01); *A61Q 19/08* (2013.01); *A61Q 19/10* (2013.01); *G01N 33/6881* (2013.01); *G06N 20/00* (2019.01); *G06Q 30/0282* (2013.01); *G16H 20/00* (2018.01); *G16H 50/20* (2018.01); *G16H 50/30* (2018.01); *G16H 50/70* (2018.01); *G16H 50/80* (2018.01); *A61B 5/411* (2013.01); *A61B 2505/05* (2013.01); *A61F 2007/0052* (2013.01); *A61N 2007/0034* (2013.01); *G01N 2800/00* (2013.01); *G06T 2207/30088* (2013.01)

(58) Field of Classification Search
CPC .......... A61K 8/00; G16H 50/30; G16H 50/70; G16H 50/20; G16H 20/00; A61B 5/441
See application file for complete search history.

(56) References Cited

U.S. PATENT DOCUMENTS

| | | | |
|---|---|---|---|
| 7,349,857 B2 | 3/2008 | Manzo | |
| 7,597,247 B2 | 10/2009 | Helmin et al. | |

(Continued)

*Primary Examiner* — Jay M. Patel
(74) *Attorney, Agent, or Firm* — Brownstein Hyatt Farber Schreck, LLP

(57) ABSTRACT

Systems and methods for generating user-specific recommendations of products or services by collaborative filtering executed and/or performed by one or more trained or untrained predictive models configured to ingest product attribute(s), product purpose(s), user location data, and/or user demographics. The predictive model(s) are leveraged to detect and determine user-specific preferences for, and preferences against, particular attributes, features, ingredients, aesthetic styles, and so on.

11 Claims, 15 Drawing Sheets

(51) Int. Cl.
 *G16H 50/20* (2018.01)
 *G16H 50/80* (2018.01)
 *G16H 50/30* (2018.01)
 *A61B 5/00* (2006.01)
 *A61F 7/00* (2006.01)
 *A61N 7/00* (2006.01)

(56) References Cited

U.S. PATENT DOCUMENTS

| | | | |
|---|---|---|---|
| 7,809,601 B2 | 10/2010 | Shaya et al. | |
| 8,388,532 B2 * | 3/2013 | Morgan | G16H 10/20 600/301 |
| 8,478,009 B2 | 7/2013 | Wei | |
| 9,789,295 B2 | 10/2017 | Zhou | |
| 10,546,658 B2 | 1/2020 | Salvi et al. | |
| 11,328,338 B1 | 5/2022 | Yuan et al. | |
| 2002/0035486 A1 | 3/2002 | Huyn et al. | |
| 2002/0038310 A1 * | 3/2002 | Reitberg | G16H 10/20 |
| 2006/0229912 A1 | 10/2006 | Negishi et al. | |
| 2006/0265244 A1 | 11/2006 | Baumann | |
| 2007/0112585 A1 * | 5/2007 | Breiter | G16H 70/60 705/2 |
| 2008/0126129 A1 | 5/2008 | Manzo | |
| 2010/0185064 A1 * | 7/2010 | Bandic | A61B 5/444 600/306 |
| 2011/0105996 A1 * | 5/2011 | Mustoe | A61K 31/366 604/20 |
| 2014/0018634 A1 * | 1/2014 | Baumann | G06Q 99/00 600/300 |
| 2014/0072583 A1 * | 3/2014 | Ardeleanu | A61P 43/00 424/172.1 |
| 2014/0188752 A1 | 7/2014 | White et al. | |
| 2014/0214709 A1 | 7/2014 | Greaney | |
| 2015/0105279 A1 * | 4/2015 | Touumazou | C12Q 1/6883 702/19 |
| 2015/0313912 A1 * | 11/2015 | Karandikar | A61K 31/555 424/488 |
| 2018/0122511 A1 * | 5/2018 | Apte | G16H 50/20 |
| 2018/0374140 A1 | 12/2018 | Stucki | |
| 2019/0012433 A1 * | 1/2019 | Conway | A61B 5/444 |
| 2019/0065970 A1 * | 2/2019 | Bonutti | G06N 20/00 |
| 2019/0213226 A1 * | 7/2019 | Ludwinski | G16H 50/20 |
| 2019/0213227 A1 * | 7/2019 | Ludwinski | A61B 5/0077 |
| 2019/0347296 A1 | 11/2019 | Parkkinen et al. | |
| 2020/0117336 A1 * | 4/2020 | Mani | F25B 49/005 |
| 2021/0027897 A1 * | 1/2021 | Rasochova | A61B 5/0077 |
| 2021/0035184 A1 * | 2/2021 | Lee | G06Q 30/0621 |

\* cited by examiner

GENERATING SKIN CARE RECOMMENDATIONS FOR A USER BASED ON SKIN PRODUCT ATTRIBUTES AND USER LOCATION AND DEMOGRAPHIC DATA

CROSS-REFERENCE TO RELATED APPLICATION

This application is a nonprovisional of and claims the benefit under 35 U.S.C. § 119(e) of U.S. Provisional Patent Application No. 62/899,127, filed Sep. 11, 2019, the contents of which are incorporated herein by reference as if fully disclosed herein.

TECHNICAL FIELD

Embodiments described herein relate to consumer product recommendation systems and, in particular, to systems and methods for generating user-specific skincare product recommendations based, at least in part, on user demographic data, product attribute data, product use/purpose data, and/or user location data. Further embodiments described herein relate to systems and methods for on-demand manufacturing of user-specific skincare products having attributes based, at least in part, on user demographic data and user location data.

BACKGROUND

Conventional consumer product or service recommendation engines typically present to users of those engines a list of consumer products that is sorted and/or filtered based solely on customer reviews or product purchase volume. More sophisticated conventional product recommendation engines provide recommendations by SKU-level collaborative filtering (e.g., user-to-user similarity determinations, item-to-item or product-to-product similarity determinations, and so on) and/or content filtering, based on user profiles or preferences.

However, these and other conventional recommendation engines, often heavily influenced by ad purchasing, are unable to account for, and are often subject to the effects of, survivorship biases of the users of those engines. In other words, conventional recommendation engines encourage a cascading/feedback effect in which a product that is recommended to users of the conventional engine, and that is eventually purchased (in part, as a result of the recommendation), is increasingly likely to be recommended by the engine again independent of the quality, value, or functionality of that product to a particular user of the engine.

This effect of conventional recommendation engines may be particularly undesirable to, and/or detrimental to, consumers purchasing nondurable or disposable goods intended for a personal purpose or use, such as cosmetic products, skincare products, hygiene products, food or drink products, clothing, cleaning products, and the like. Such users of a conventional recommendation engine often find that recommendations provided by that engine are not suitable for them, as different users present with different medical, dietary, and/or dermatological needs or requirements, present with different allergies to different materials or ingredients, have different preferences for the presence or absence of particular features or ingredients or additives, and so on.

SUMMARY

Generally and broadly, embodiments described herein reference systems and methods for generating user-specific recommendations of products (or services) by collaborative filtering executed and/or performed by one or more trained or untrained predictive models configured to ingest product attribute(s), product purpose(s), user location data, and/or user demographics. In these constructions, the predictive model(s) described herein can be leveraged to detect and determine user-specific preferences for and/or preferences against particular attributes, features, ingredients, aesthetic styles, and so on which, in turn, can be used to select a product or service from a set of product or services most suitable to the user or, alternatively, can be used to inform production of a custom-tailored product or service or, alternatively or additionally, can be used to inform the user of one or more features, attributes or ingredients that the user should avoid.

An example embodiment described herein, which is not exhaustive of the various use cases for the embodiments described herein, includes a server, referred to herein as a "host server," configured to correlate (1) demographic data, (2) skin condition or characteristic data (collectively, both skin conditions and skin characteristics are referred to as "skin concerns") and/or (3) diagnosis data associated with a user of that system (referred to herein as the "user") to sets of active and inactive ingredients therapeutic or otherwise beneficial to one or more skin concerns that the user likely presents and/or sets of active and inactive ingredients that can be used for non-therapeutic purposes (e.g., cosmetics, makeup removers, cleansers, and so on). These examples are not exhaustive of the configurations or purposes of a system such as described herein; other constructions and system architectures are possible.

For example, an embodiment described herein relates to a method of operating a host server coupled to a client device. The client device is configured to be operated by a user. The host server communicates with the client device and is configured to diagnose or otherwise identify one or more skin concerns of the user and, additionally, to identify a treatment or suitable skincare ingredient for those identified skin concerns.

Such methods may include an operation of receiving a user dataset at the host server. The user dataset is received from the client device and can be supplied in whole or in part by the user. In other examples, metadata or other demographic, geographic, or third-party data can be collected by the client device and bundled with a user input to generate the user dataset. The user dataset can be submitted in any form or format and may include encrypted or unencrypted data. In many embodiments, the user data is encrypted and presented in a structured data format such as, but not limited to: javascript object notation; extensible markup language; structured query language query format; and so on. This listing of possible structured formats is not exhaustive.

Once the user dataset is received by the host server, the host server can iterate through a set of skin concerns which, as noted above, can include skin conditions (e.g., rosacea, dermatitis, melasma, vitiligo, and so on) or characteristics (e.g., light sensitivity, chemical sensitivity, abrasive sensitivity, propensity for blemishes, propensity for hyperpigmentation, and so on). Thereafter, the host server can query a database service to retrieve a set of diagnostics associated with each skin concern. The diagnostics can include data representing one or more signs (objective information such as color, temperature, user ethnicity or sex, and the like) and/or symptoms (subjective information such as pain sensation or sensitivity and the like) that inform a diagnosis of or identification of a particular skin concern.

Thereafter, the host server can iterate through each diagnostic to determine a credibility metric. The credibility metric represents a likelihood that, based on the user dataset, a given diagnostic is true for a given user.

Once the host server has determined a credibility metric for each diagnostic associated with a given skin concern, it can determine a confidence metric representing a likelihood that the user exhibits and/or presents the given skin concern.

Once the host server has determined one or more skin concerns that have a predicted high confidence metric, the host server can optionally query the database service to retrieve a skin concern co-occurrence dataset.

Thereafter, a predictive model service of the host server or another computing device can ingest the user dataset, each confidence metric, and the skin concern co-occurrence dataset to determine which among the high confidence skin concerns or characteristics are likely to, or can, co-present or co-occur in the same user. More specifically, the host server can receive from the predictive model a diagnosis indicating a set of one or more co-occurring skin concerns predicted by the system to be exhibited by the user. With this information, the host server can iterate through each skin concern of the set to query the database service to retrieve a list of therapeutic or otherwise beneficial active ingredients.

Thereafter, once the host server has obtained a list of beneficial active ingredients that can exhibit therapeutic or otherwise beneficial effects for the user, the host server can communicate a treatment recommendation to the client device, the treatment recommendation based on each list of therapeutic or otherwise beneficial active ingredients.

Embodiments described herein include or reference a configuration in which the user dataset includes (1) a first data item with an input (e.g., answers to an adaptive diagnostic survey) provided directly by the user to the client device, (2) a second data item with a geographic location of the user, and (3) a third data item with a demographic of the user (e.g., an age, a sex, or an ethnicity, pregnancy condition, postpartum condition, menopausal condition, and so on).

Some embodiments described herein configure the host server to query the database service and/or the predictive model service to retrieve a treatment modification based on the geographic location of the user. Example treatment modifications can be based on, without limitation: a local area pollution; a local area humidity; a local area water hardness; a local area seasonal temperature average; a local area seasonal ultraviolet light exposure average; and so on. In these examples, the treatment recommended to the user can be based, at least in part, by the treatment modification.

Some embodiments described herein configure the host server to query the database service to retrieve an active ingredient interaction dataset. In these examples, the active ingredient interaction dataset can be ingested by the predictive model service along with each list of therapeutic or otherwise beneficial active ingredients. Thereafter, the predictive model service can output a set of non-interacting therapeutic or otherwise beneficial active ingredients which can be used by the host server to inform the treatment recommendation.

Other embodiments described herein include or reference a configuration in which a treatment recommendation includes a treatment application type selected from a set of treatment application types such as, but not limited to: a facial cleanser; a topical sunscreen; a topical serum; an exfoliator; a moisturizer; a chemical peel; a toner; an eye cream; a night cream; and so on.

Additional embodiments described herein relate to a method of operating a host server to generate training data to train a customer review prediction model configured to output a predicted likelihood of a positive-sentiment review of a consumer product when the consumer product is used as treatment for a specified medical condition. Such embodiments can include the operations of: obtaining, by the host server, web page text content served by a web server in communication with the host server, the web page text content containing a customer review; extracting, by the host server, text associated with the customer review from the web page text content; identifying, by the host server, a consumer product referenced by the customer review from the extracted text; identifying, by the host server, a medical condition referenced by the customer review from the extracted text; identifying, by the host server, an author of the customer review from the extracted text; extracting, by the host server, a scaled rating of the consumer product by the author of the customer review from the extracted text; determining, by the host server, demographic information of the author of the customer review from the extracted text; querying, by the host server, a product database to obtain an ingredient list of the consumer product; inserting, by the host server, into a predictive model training data database in communication with the host server the consumer product, the medical condition, the author of the customer review, the demographics of the author, the scaled rating of the consumer product, and the ingredient list; and, finally, initiating a process to train the predictive model from the predictive model training data database.

Related embodiments described herein further include: filtering, by the host server, the ingredient list into an active ingredient list and an inactive ingredient list; determining, by the host server, for each respective ingredient of the ingredient list, a respective estimated ingredient percentage by volume; and inserting, by the host server, into the predictive model training the active ingredient list with estimated ingredient percentage by volume, and the inactive ingredient list with estimated ingredient percentage by volume.

Related embodiments described herein include or reference a configuration in which determining each respective estimated ingredient percentage by volume may be based on an ordering of the ingredient list. For example, the host server can be configured to access a third party database (e.g., a governmental or regulatory body, such as the Food and Drug Administration) to determine an ingredient listing and ordering.

Related embodiments described herein may include an operation of filtering the inactive ingredient list to exclude ingredients not associated with allergic reactions and not associated with drug interactions. For example, water or glycerin may be listed as ingredients and may not be known to be associated with any allergy or any drug interaction. As such, it may not be necessary to train the customer review prediction model with such common and non-interactive (e.g., high biocompatibility) ingredients.

Further embodiments described herein include an operation of performing, by the host server, a sentiment analysis on at least a portion of the extracted text, and inserting, by the host server, into the predictive model training a data item based on the sentiment analysis that corresponds to whether the customer review is associated with a positive treatment experience, a neutral treatment experience, or a negative treatment experience.

Other related embodiments described herein relate to a method of training a diagnostic prediction model. In these examples, the method can include the operations of: receiving as input a customer review of a consumer product;

identifying a skin concern referenced by the customer review; determining a user dataset by extracting demographic information of an author of the customer review from the customer review; determining by sentiment analysis a sentiment indication of the consumer review corresponding to whether the customer review exhibits a positive sentiment, a neutral sentiment, or a negative sentiment; inserting into a diagnostic prediction model data database the skin concern, the user dataset, and the sentiment of the consumer review; and training the diagnostic prediction model on the diagnostic model data database to output a predicted likelihood that a given input user dataset corresponds to a user that exhibits the skin concern.

Related embodiments described herein include or reference a configuration in which the method additionally receives as input medical research data. In these examples, the method can be configured to (1) identify a second skin concern referenced by the medical research data, (2) identify user demographic data referenced by the medical research data and (3) insert into the diagnostic prediction model data database the second skin concern and the user demographic data. Thereafter, the method can advance to train the diagnostic prediction model on the diagnostic model data database.

Other embodiments described herein relate to methods of manufacturing a custom skincare product. In one example, a method described herein includes operations of: receiving as input an active ingredient list; selecting a skincare base from a set of skincare bases; selecting one or more skincare additives based on the active ingredient list; combining the selected skincare base and the selected one or more skincare additives; and packaging the combined selected skincare base and the selected one or more skincare additives as the custom skincare product.

In another example, a method described herein includes operations of: receiving as input user demographic data and a user skin concern; ingesting the input by a predictive model to obtain an active ingredient list based on the user skin concern and the user demographic data; selecting a skincare base from a set of skincare bases; selecting one or more skincare additives based on the active ingredient list; combining the selected skincare base and the selected one or more skincare additives; and packaging the combined selected skincare base and the selected one or more skincare additives as the custom skincare product.

In these and related embodiments, the user demographic data can include allergy information, medication information, and user preference information. User preference information can include one or more of: a user preference (e.g., prefers or does not prefer) regarding an ingredient type (e.g., oils, acids, emulsifiers, fragrances, colors, and so on); a user preference regarding an ingredient source (e.g., organic, sustainably-sourced, plant-based, originating from recycled material, and so on); or a user preference regarding an environmental impact of an ingredient (e.g., sustainability of manufacturing, carbon footprint, raw material sourcing, and so on).

In these and related embodiments, the user-specific active ingredient list can be filtered based on the user demographic data or a geographic location of the user. In other cases, at least one of the skincare base or the one or more skincare additives are filtered based on the user demographic data.

Further embodiments can include the operation of ingesting (1) the input (e.g., the user demographic data and a user skin concern) and (2) the diagnosis of one or more likely skin concerns by the customer review prediction model to obtain a user-specific inactive ingredient list statistically likely to elicit a positive product review from the user. In these examples, the user-specific inactive ingredient list is based at least in part on the user skin concern and the user demographic data. In these examples, the method can advance by selecting one or more skincare additives based on the user-specific inactive ingredient list. In these embodiments, the method can combine the selected skincare base, the active ingredient additives, and the inactive ingredient additives. In these examples, the user-specific inactive ingredient list can include at least one or more of a colorant, a scent, a filler, an emulsifier, a preservative, an abrasive additive, or an oil.

In another example, a method of manufacturing described herein can include operations such as: receiving as input user demographic data and a user skin concern; ingesting the input by a customer review prediction model to obtain a user-specific active ingredient stop list statistically likely to elicit a negative product review from the user based on the user demographic data and the user skin concern; selecting a skincare base from a set of skincare bases; selecting one or more skincare additives that do not contain any ingredient on the user-specific active ingredient stop list; combining the selected skincare base and the selected one or more skincare additives; and packaging the combined selected skincare base and the selected one or more skincare additives as the custom skincare product.

In these and other embodiments, the one or more skincare additives comprise a prescription strength active ingredient. In such examples, the method may further include an operation such as submitting a request for dermatologist or pharmacist approval prior and awaiting said approval prior to combining the selected skincare base and the selected one or more skincare additives.

Other embodiments described herein relate to a method of generating a user-specific unique identifier associated with a custom set of skincare products. More specifically, the method can include operations such as: receiving as input user demographic data and a user survey result; ingesting the input by a diagnostic predictive model to obtain a diagnostic matrix each entry of which corresponds to a statistical likelihood of a true diagnosis of a respective one skin concern; and generating the user-specific unique identifier from the diagnostic matrix.

In these examples, generating the user-specific unique identifier from the diagnostic matrix can include flattening the diagnostic matrix into a single row. Thereafter, the row can be hashed to generate a unique value. Alternatively, the operation of generating the user-specific unique identifier from the diagnostic matrix can include calculating a hash value (using any suitable technique, formula, or algorithm) of the diagnostic matrix.

In such examples, the user-specific unique identifier can be inserted (with, optionally, the user demographic data) into a customer history database configured to track changes in a diagnostic matrix associated with a specific user over time.

BRIEF DESCRIPTION OF THE DRAWINGS

Reference will now be made to representative embodiments illustrated in the accompanying figures. It should be understood that the following descriptions are not intended to limit this disclosure to one included embodiment. To the contrary, the disclosure provided herein is intended to cover alternatives, modifications, and equivalents as may be included within the spirit and scope of the described embodiments, and as defined by the appended claims.

The use of the same or similar reference numerals in different figures indicates similar, related, or identical items.

Figure 1:
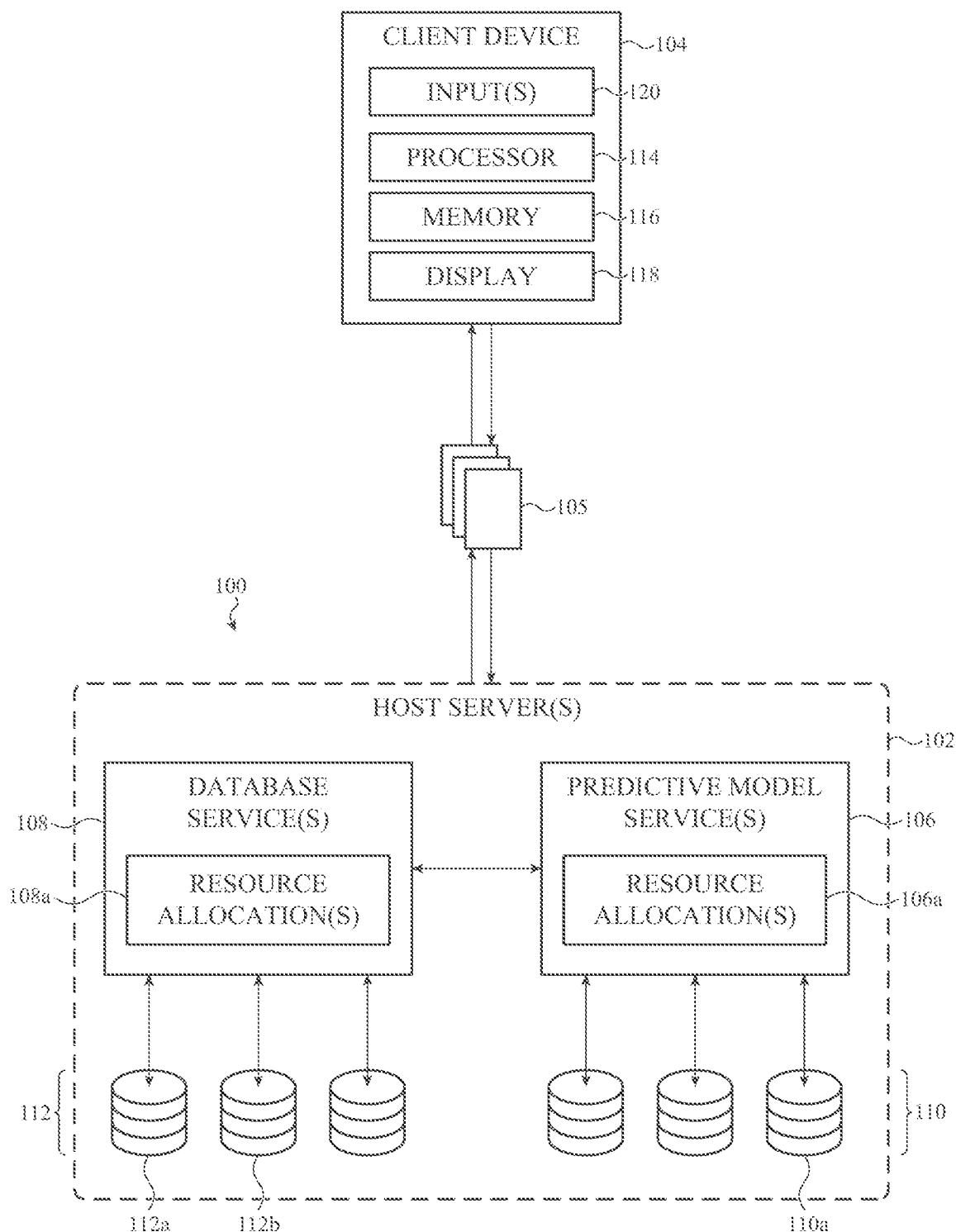
FIG. 1 is a schematic representation of a client-server architecture of a system, such as described herein.

Additionally, it should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Embodiments described herein reference systems and methods for generating user-specific skincare products and recommendations by leveraging outputs of one or more predictive models configured to ingest attributes of existing skincare products (e.g., ingredients, ingredient proportions, and so on), skincare customer reviews, medical and/or dermatological data, user location data, self-reported user skin concern information, and/or user demographics.

An example embodiment described herein includes a server, referred to herein as a "host server," configured to correlate (1) demographic data, (2) skin concern data, and/or (3) diagnosis data associated with a user of that system (referred to herein as the "user") to sets of active and inactive ingredients therapeutic or otherwise beneficial to one or more skin concerns (including either or both skin conditions and skin characteristics or properties) that the user likely presents or exhibits. It is appreciated, however, that these examples are not exhaustive of the configurations or purposes of a system such as described herein; other constructions and system architectures are possible. More specifically, it may be appreciated that a system described herein can be trained and/or configured to provide recommendations of non-skincare products, services, or any other suitable durable or non-durable good.

In particular, a system described herein is configured to operate a host server to collect information from a user that may be useful to diagnose one or more skin concerns exhibited by the user. This data is collectively referred to herein as "user data" and/or a "user dataset." For example, in many embodiments, the host server may communicably couple to a client device operated by the user in order to present the user with a questionnaire.

The user's responses to the questionnaire, along with other demographic and/or geographic data of the user can be consumed by a "predictive model." As used herein, the phrase "predictive model" refers to any hardware, software, or other circuit or processor or combination thereof configured to execute any suitable pattern recognition or classification algorithm, probabilistic model, artificial intelligence method, untrained or trained learning algorithms (e.g., supervised or unsupervised learning, reinforcement learning, feature learning, sparse dictionary learning, anomaly detection, or association rules, the like). These learning algorithms may utilize a single or any suitable combination of various models such as artificial neural networks, decision trees, support vector networks, Bayesian networks, genetic algorithms, or training models such as federated learning.

A "diagnostic" predictive model, is a predictive model trained and/or otherwise configured to output a metric (or matrix, array, dictionary, list, or set of metrics) corresponding to a statistical likelihood that a given user exhibits a particular skin condition or characteristic. For example, a diagnostic predictive model may be configured to output a matrix, which can be referred to as a diagnostic matrix. The diagnostic matrix can include a number of entries, each associated with a particular skin condition or characteristic. In this architecture, the value of each entry of the diagnostic matrix is a statistical likelihood that the user exhibits the associated skin condition or characteristic.

In many embodiments, the diagnostic predictive model is trained by scraping information from customer reviews and other data sources (e.g., scientific journal publications, transcripts of video reviews, blog posts, and so on) available to the general public. More specifically, in many examples, a review author's demographics (e.g., age, sex, ethnicity, and so on) and geographic data (e.g., when the review was authored, where the author lives, and so on) can be extracted from review content and/or a profile page of that author along with a rating (e.g., a star rating) and information or data about the product(s) that are the subject of the review. In addition, skin concern and/or skin diagnosis information can be extracted from a body and/or title or other content of the review. Likewise, ingredient information, including both active ingredients and inactive ingredients, can be obtained once one or more products that are the subject of the review are identified. In many embodiments, ingredient content by volume can be estimated based on an order in which the ingredients are presented and/or from literature associated with the identified product that may be supplied by a manufacturer of the product (e.g., instructions for use, marketing materials, and so on) or by a third party (e.g., a regulatory body, such as the Food and Drug Administration). Further, a sentiment analysis operation can be performed to determine a positive sentiment, a neutral sentiment, or a negative sentiment by the author of the review. Once the foregoing data items, and/or other data which may be obtained from other databases or from the review content, are obtained, such data can be inserted into a training data database table (or other data structure) in order to train the diagnostic predictive mode to determine correlations between positive and/or negative use experiences, user demographics, user skin concerns, and specific ingredients commonly found in retail or prescription skincare products.

After the user data and/or the user geographic data are consumed by the predictive model, the predictive model may output a matrix or other data structure including one or more entries, each of which corresponds to a prediction (e.g., a statistical likelihood) of whether the user presents with a specific skin concern associated with that entry. This matrix is referred to herein as a "diagnostic matrix."

Thereafter, the diagnostic matrix and/or the user demographic data (along with the geographic data) can be consumed by another predictive model, trained from the same or different data used to train the diagnostic predictive model, to obtain a list of ingredients (and/or therapies, and/or other therapeutic or otherwise beneficial interventions) that are likely to elicit a positive product review from the user or, in another phrasing, likely to address one or more likely skin concerns referenced in the diagnostic matrix. This listing of ingredients, which can include active ingredients and inactive ingredients, can be filtered at least in part in view of information gathered by the system after querying one or more: drug interaction databases; ingredient interaction databases; medical interaction databases; user preference profiles or databases; and so on.

Once a user-specific ingredient listing is obtained, systems and methods described herein can be configured to manufacture a custom skincare product containing at least a threshold number of those ingredients. The product can be prepared by selecting a skincare base (or bulk) from a set of skincare bases and mixing that base with one or more skincare additives that may be discrete ingredients or combinations of commonly copresent ingredients.

In certain embodiments, custom skincare products such as those described herein can be modified based on a user's location. For example, moisture content in a custom moisturizer may be different for users ordering custom products from high humidity geographies than for users ordering custom products from low humidity geographies. Custom skincare products, such as those described herein, can be customized to individual users further by leveraging data related to: local weather; a time of year or season; local water hardness; local or municipal water additives; local ultraviolet index; local pollution metrics; local air quality metrics; and so on. In this manner, as a user moves from place to place or as seasons change, custom skincare products, which may address similar or identical skincare conditions, may be differently customized for a given user.

In some embodiments, custom skincare products such as those described herein can be modified and/or customized based on changing needs of a given user. For example, as a skin concern or concern of a user is addressed, that user's skincare product needs may correspondingly change. Similarly, as noted above, as seasons change and/or local weather or water hardness changes, a user's skincare product needs may correspondingly change. Embodiments described herein are configured to provide custom skincare based on time or season of year, user-specific needs, user geographic information, and the like.

These foregoing and other embodiments are discussed below with reference to FIGS. 1-13. However, those skilled in the art will readily appreciate that the detailed description given herein with respect to these figures is for explanatory purposes only and should not be construed as limiting.

FIG. 1 is a schematic representation of an example recommendation engine, such as described herein. In the illustrated embodiment, the recommendation engine 100 is implemented with a client-server architecture including a host server 102 that communicably couples (e.g., via one or more networking or wired or wireless communication protocols) to one or more client devices, one of which is shown as the client device 104. The client device 104 and the host server 102 of the recommendation engine 100 can be configured to transact information, identified as the data items 105, such as, but not limited to: user demographic data; user geographic data; and so on.

It may be appreciated that other client devices may be configured in a substantially similar manner as the client device 104, although this may not be required of all embodiments and different client devices can be configured differently and/or may transact data or information with, and/or provide input(s) to, the host server 102 in a unique or device-specific manner.

The client device 104 can be any suitable personal or commercial electronic device and may include, without limitation or express requirement, a processor, volatile or non-volatile memory, and a display. Example electronic devices include, but are not limited to: laptop computers; desktop computers; wearable devices; cellular phones; tablet computing devices; and so on. It may be appreciated that a client device 104, such as described herein, can be implemented in any suitable manner.

In many embodiments, the processor of the client device 104 can be configured to execute an application (herein referred to as a "client application") stored, at least in part, in memory. The client application is configured to access and communicate with the host server 102 and to securely transact information or data with, and provide input(s) to, the host server 102. In some embodiments, the client application may be a browser application configured to access a web page or service hosted by the host server 102 that is accessible to the client device 104 over a private or public network that may, in some embodiments, include the open internet.

In many embodiments, the host server 102 is configured to operate within or as a virtual computing environment that is supported by one or more physical servers including one or more hardware resources such as, but not limited to (or requiring) one or more of: a processor; a memory; non-volatile storage; networking connections; and the like. For simplicity of description and illustration, these example hardware resources are not shown in FIG. 1.

In many embodiments, the host server 102 can include a number of discrete subservices or purpose-configured modules, containers, or virtual machines each configured to perform, coordinate, serve, or otherwise provide one or more services, functions, or operations of the host server 102, such as (1) serving a questionnaire to a user operating the client device 104, (2) receiving a response from the client device 104 containing user data (e.g., geographic data, questionnaire responses, demographic data, preference data and so on), (3) determining a diagnosis of one or more skin concerns presented by the user by leveraging a predictive model trained by information obtained from at least customer review data scraped from a public resource, (4) determining a user-specific ingredient list by leveraging a predictive model trained by information obtained from at least customer review data scraped from a public resource, and (5) determining or selecting a skincare product base and one or more skincare product additives that can be mixed together to create a user-specific skincare product. In addition, the host server 102 can be configured to generate training data and to train the one or more predictive models.

To perform these and other operations, the host server 102 of the recommendation engine 100 can include one or more purpose-configured modules or services. For example, in many embodiments, the host server 102 includes a predictive model service 106 and a database service 108, which may be communicably coupled to each other and/or to one or more other services or functional elements of the host server 102 (not shown).

The predictive model service 106 of the host server 102 can be configured to host and/or otherwise service requests to access one or more predictive models that may be trained in a particular manner and/or may serve a particular function. For example, as described herein, the predictive model service 106 can be configured to provide access to a diagnostic predictive model configured to ingest a user dataset and to output a diagnostic matrix, entries of which correspond to a probabilistic assessment of a likelihood that the particular user presents with a given or particular skin concern. In other cases, the predictive model service 106 may also be configured to provide access to a consumer review predictive model configured to ingest a diagnostic matrix, a user dataset and/or other information, and to output a customer review prediction matrix, entries of which correspond to a probabilistic assessment of likelihood that a particular ingredient, if used by the user in a recommended manner, would elicit a positive product review from that user. In still further embodiments, the predictive model service 106 can be configured to provide access to other predictive models, trained in any suitable manner. In many cases, a predictive model served by the predictive model service 106 of the host server 102 can be stored in any suitable form or format in a database accessible to the predictive model service 102, such as the databases 110, one of which is identified as the model database 110*a*. The predictive model service 106 and the various functions and operations thereof is described in greater detail with reference to embodiments that follow.

The database service 108 of the host server 102 can be configured to host and/or otherwise service requests to access to one or more databases or data sources, internal or external to the host server 102. Example databases, access to which is facilitated and/or controlled by the database server 108 are illustrated as the databases 112 and can include, without limitation: an ingredient interaction database 112*a*; a drug interaction database 112*b*; an ingredient database; a product database; a customer review database; a scientific journal or study information database; and so on. In many cases, the database service 108 of the host server 102 can be configured to access one or more remote or third party databases to obtain information. An example of a third party database that may be accessed by a database service, such as described herein, includes: a water hardness database; a weather prediction database; a customer database; a customer review database; a scientific journal or study database; and the like. The database service 108 and the various functions and operations thereof is described in greater detail with reference to embodiments that follow.

Each of the predictive model service 106 and the database service 108 are associated with allocations of physical or virtual resources (identified in the figure as the resource allocations 106*a* and 108*a* respectively), such as one or more processors, memory, and/or communication modules (e.g., network connections and the like), that such an implementation is not required. More generally, it may be appreciated that the various functions described herein of a host server 102 can be performed by any suitable physical hardware, virtual machine, containerized machine, or any combination thereof. Similarly, it may be appreciated that the client device 104 can be implemented in a number of suitable ways. In one embodiment, the client device 104 includes a processor 114, a memory 116, a display 118, and an input sensor or input device 120. These components can cooperate to perform or coordinate one or more operations of the client device 104 as it communicates with and transacts information with the host server 102.

The foregoing embodiment depicted in FIG. 1 and the various alternatives thereof and variations thereto are presented, generally, for purposes of explanation, and to facilitate an understanding of various configurations and constructions of a system, such as described herein. However, it will be apparent to one skilled in the art that some of the specific details presented herein may not be required in order to practice a particular described embodiment, or an equivalent thereof.

Figure 2:
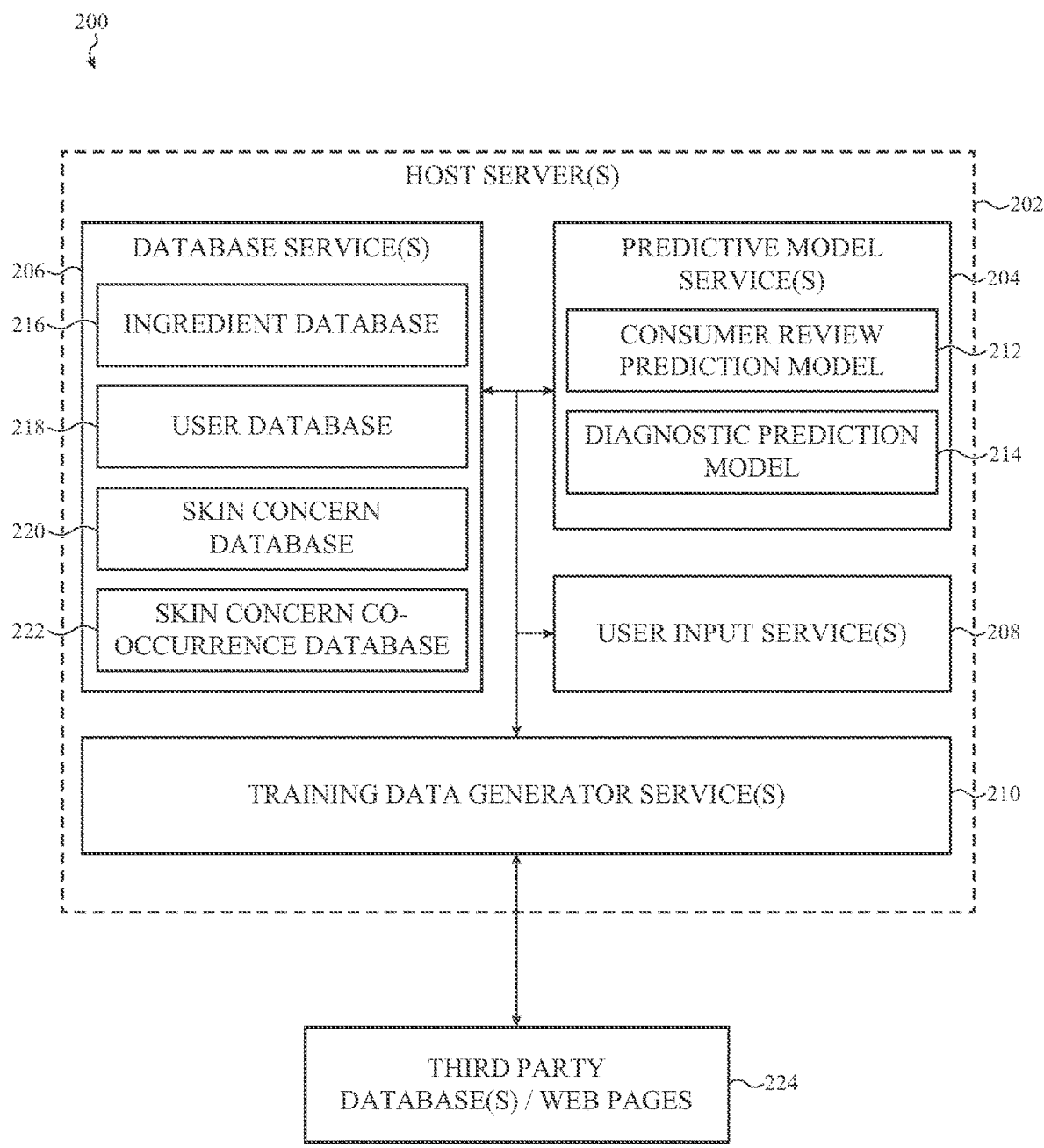
FIG. 2 is a schematic representation of a host server of the client-server architecture of the system of FIG. 1.

FIG. 2 is a schematic representation of a host server of the client-server architecture of the system of FIG. 1. In this embodiment, the recommendation engine 200 includes a host server 202 which, in turn, is defined by a number of discrete and purpose-configured components. In particular, the host server 202 can include a predictive model service 204, a database service 206, a user input service 208, and a training data generator service 210.

As noted with respect to other embodiments described herein, the predictive model service 204 of the host server 202 can facilitate access to and data transactions with one or more predictive models, such as a consumer review prediction model 212 and a diagnostic prediction model 214.

As noted with respect to other embodiments described herein, the consumer review prediction model 212 can be configured, in some embodiments, to perform an operation to assess a statistical likelihood that a particular ingredient, if used by a particular user, is likely to elicit a positive review from that user with respect to a skin concern of that user. As noted above, the consumer review prediction model 212 can be trained with data extracted from one or more public and/or private databases comprising consumer reviews of skincare products. In particular, the consumer review prediction model 212 can be trained to determine correlations between demographic and geographic data associated with an author of a review, the ingredient set of a product that is the subject of that review, and one or more skin concerns or conditions mentioned in that review. Once trained on a sufficiently large dataset, the consumer review prediction model 212 can predict whether a given user exhibiting a skin concern is likely to successfully treat the condition associated with a specific ingredient. The various functions and operations of a consumer review prediction model, such as the consumer review prediction model 212 depicted in FIG. 2 are described in greater detail below.

Similarly, the diagnostic prediction model 214 can be configured, in some embodiments, to perform an operation to assess a statistical likelihood that a particular user dataset consumed by the model corresponds to a user that presents with a specific given skin concern. More generally, the diagnostic prediction model 214 can be configured to output a diagnostic matrix, each entry of which corresponds to a statistical assessment or prediction of a likelihood that a skin concern associated with that particular entry is presented by a given user. As noted above, the diagnostic prediction model 214 can also be trained with data extracted from one or more public and/or private databases comprising consumer reviews of skincare products (and/or scientific journal or study data). In particular, the diagnostic prediction model 214 can be trained to determine correlations between demographic and geographic data associated with an author of a review and one or more skin concerns or conditions mentioned in that review. Similar to the consumer review prediction model 212, once trained on a sufficiently large dataset, the diagnostic prediction model 214 can predict whether a given user exhibits or is likely to present with one or more skin concerns. The various functions and operations of a consumer review prediction model, such as the diagnostic prediction model 214 depicted in FIG. 2, are described in greater detail below.

As noted with respect to other embodiments described herein, the database service 206 of the host server 202 can facilitate access to, and data transactions with, one or more databases such as, but not limited to: an active and/or inactive ingredient database 216; a customer database 218; a skin concern database 220; and/or a skin concern co-occurrence database 222.

In one embodiment, the active and/or inactive ingredient database 216 is configured to store information related to ingredients that may be used in one or more skincare products, whether customized or otherwise. Information contained in the active and/or inactive ingredient database 216 can include, but may not be limited to: an ingredient name; an ingredient identifier; an ingredient status identifier (e.g., active or inactive); an ingredient source; an environmental impact metric of an ingredient; a price per unit of the ingredient; allergy information associated with the ingredient; interaction information associated with the ingredient; an ingredient description; a list or identifier of a skin concern for which the ingredient is therapeutic or otherwise beneficial; and so on and the like.

The customer database 218 can be configured in any suitable manner to store user data and/or demographic data or geographic data. Examples include, but are not limited to: a user name; a user age; a self-reported user skin type; a user skin concern (or set of skin concerns or unique identifier corresponding to a set of skin concerns); an ethnicity or set of ethnicities; a geographic location of the user; and so on. In many cases, the customer database 218 can store historical information as well, noting and recording changes in a user's skincare recommendations and/or changes in demographic or geographic data over time.

The skin concern database 220 can be configured in any suitable manner to store information related to skin concerns that can be diagnosed by the recommendation engine 200 or, more particularly, the diagnostic prediction model 214 of the predictive model service 204 of the host service 202. In many embodiments, the skin concern database 220 is configured to store, without limitation: a skin concern identifier; a skin concern sign list; a skin concern symptom list; a set of one or more diagnostics that, if exhibited by a user, increase a statistical likelihood that the user exhibits the skin concern; and so on.

The skin concern co-occurrence database 222 can be configured in any suitable manner to store information related to statistical likelihoods of a particular skin concern occurring with another skin concern based on population data and/or demographic data of users exhibiting said conditions. In this configuration, the skin concern co-occurrence database 222 can be leveraged by the host service 202 to determine which diagnosis among a set of diagnoses output by the diagnostic prediction model 214 via a diagnostic matrix are more likely to be correct diagnoses than others.

The training data generator service 210 of the host server 202 can be configured to iteratively or otherwise obtain training data to update training of one or more of the models of the predictive model service 204. In particular, in many embodiments, the training data generator service 210 is configured to scrape information from publicly-accessible consumer review and/or scientific dermatological study/survey databases (collectively identified as the third party databases 224) and to extract data from those databases to generate training data that correlates particular demographic characteristics (of the authors of customer reviews and/or of the subject(s) of scientific studies) and one or more therapeutic or otherwise beneficial active or inactive ingredients of the product(s) that are the subject of those reviews/studies. The various functions and operations of a training data generator service, such as the training data generator service 210 depicted in FIG. 2 are described in greater detail below.

It may be appreciated that the foregoing description of FIG. 2, and the various alternatives thereof and variations thereto, are presented, generally, for purposes of explanation, and to facilitate a thorough understanding of various possible configurations of a recommendation engine, such as described herein. However, it will be apparent to one skilled in the art that some of the specific details presented herein may not be required in order to practice a particular described embodiment, or an equivalent thereof. For example, it may be appreciated that the host service 202 depicted in FIG. 2 can be configured to transact information with the client device 104 to provide recommendations to a user operating the client device 104 in a number of suitable ways.

Figure 3A:
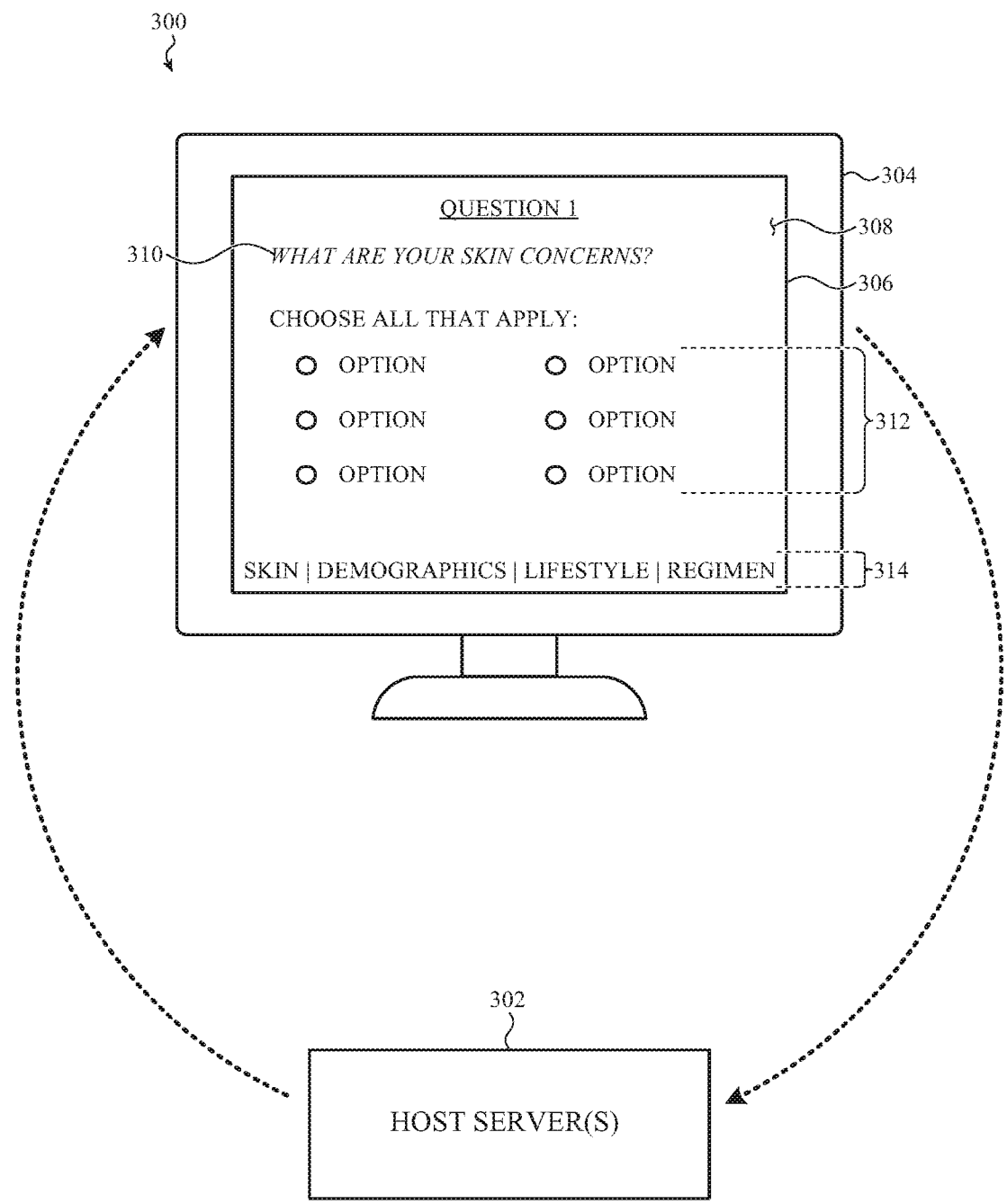
FIG. 3A is a signal/process flow diagram depicting a client device in communication with the host server of FIG. 2 and rendering a sample graphical user interface configured to solicit input from a user of the client device so that the host server can provide a recommendation to that user.

For example, FIG. 3A is a signal/process flow diagram depicting a client device in communication with the host server of FIG. 2 and rendering a graphical user interface configured to solicit input from a user of the client device so that the host server can provide a recommendation to that user. In particular, in this embodiment, the recommendation engine 300 includes a host service 302 in communication with a client device 304. The client device 304 includes a display 306 that renders a graphical user interface 308. In this example, the graphical user interface 308 renders a portion of a questionnaire that can be served to the client device 304 to solicit user information from a user operating the client device 304. In this embodiment, the graphical user interface 308 can present a question 310 to the user. In response to the question 310, the user may select one or more options, such as the options 312 to provide demographic information to the host service 302 such that the host service 302 can provide a recommendation for a skincare product to the user. The question(s) asked of the user by the host service 302 can thematically vary (see, e.g., the questionnaire sections 314). For example, as depicted in FIG. 3A, questions can be asked of the user related to the user's skin concern and/or concerns, user demographics, user lifestyle (e.g., activity level, outdoor activity, swimming activity, and so on); user skincare regimen, and so on.

Figure 3B:
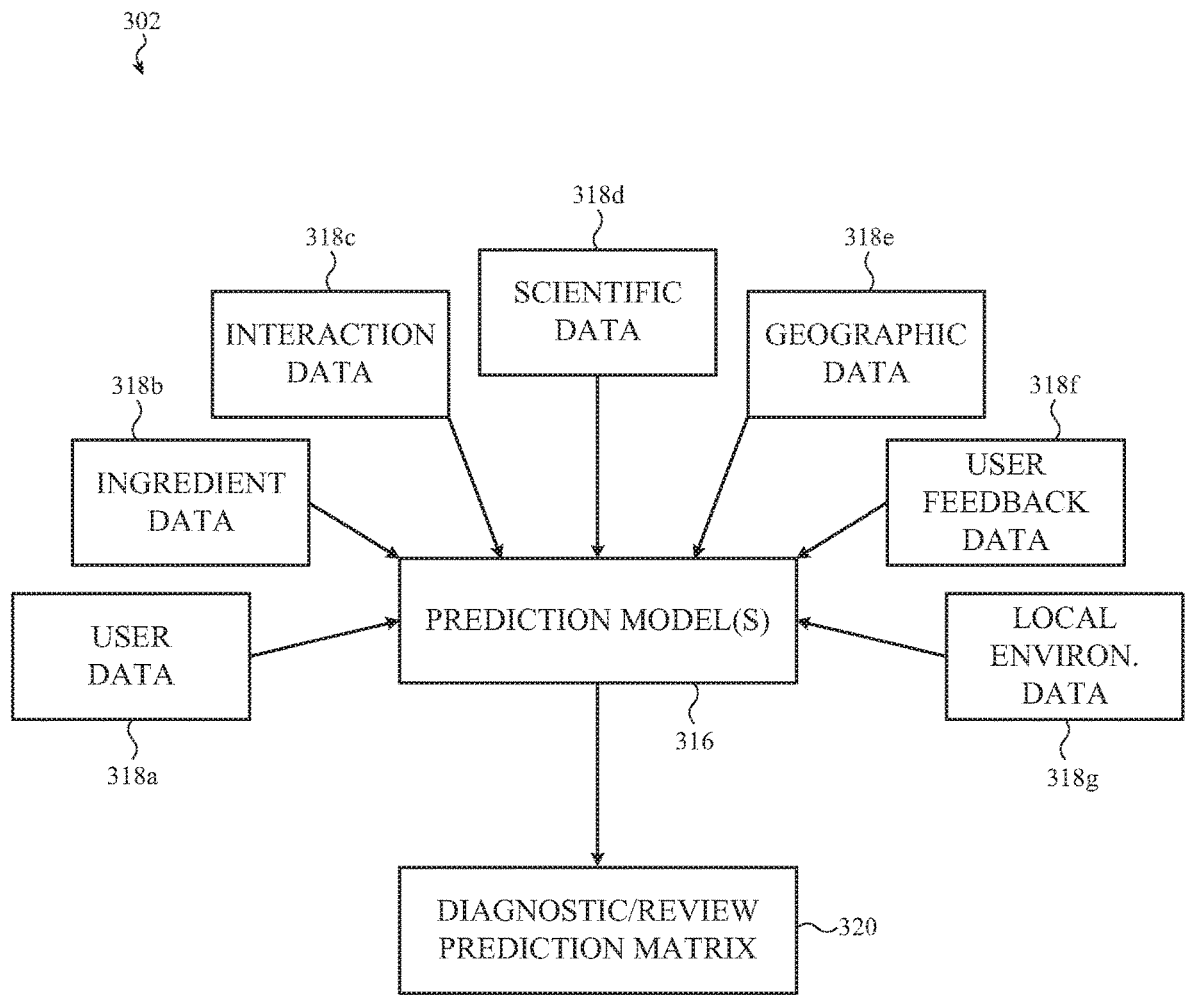
FIG. 3B is a signal/process flow diagram depicting data source(s) accessible to the host server of FIG. 3A that can supply information or data to a predictive model to ingest to provide a recommendation to the user.

More specifically, the host server 302 can be configured to consume data from a variety of sources in order to generate one or more recommendations for the user. FIG. 3B is a signal/process flow diagram depicting data source(s) accessible to the host server of FIG. 3A that can supply information or data to a predictive model to ingest to provide a recommendation to the user. In this example, the host service 302 includes a prediction model 316 that can receive data from a variety of sources, in any suitable form and format, such as a patient data datasource 318a, an ingredient data datasource 318b, an ingredient interaction data database 318c, a scientific data datasource 318d, a geographic data datasource 318e, a customer feedback data datasource 318f, a local environment data datasource 318g, and so on. Once the prediction model 316 consumes data retrieved from one or more of these datasources (or other data sources), the prediction model 316 can output a prediction matrix 320, which may be a diagnostic prediction matrix or a customer review prediction matrix.

Figure 3C:
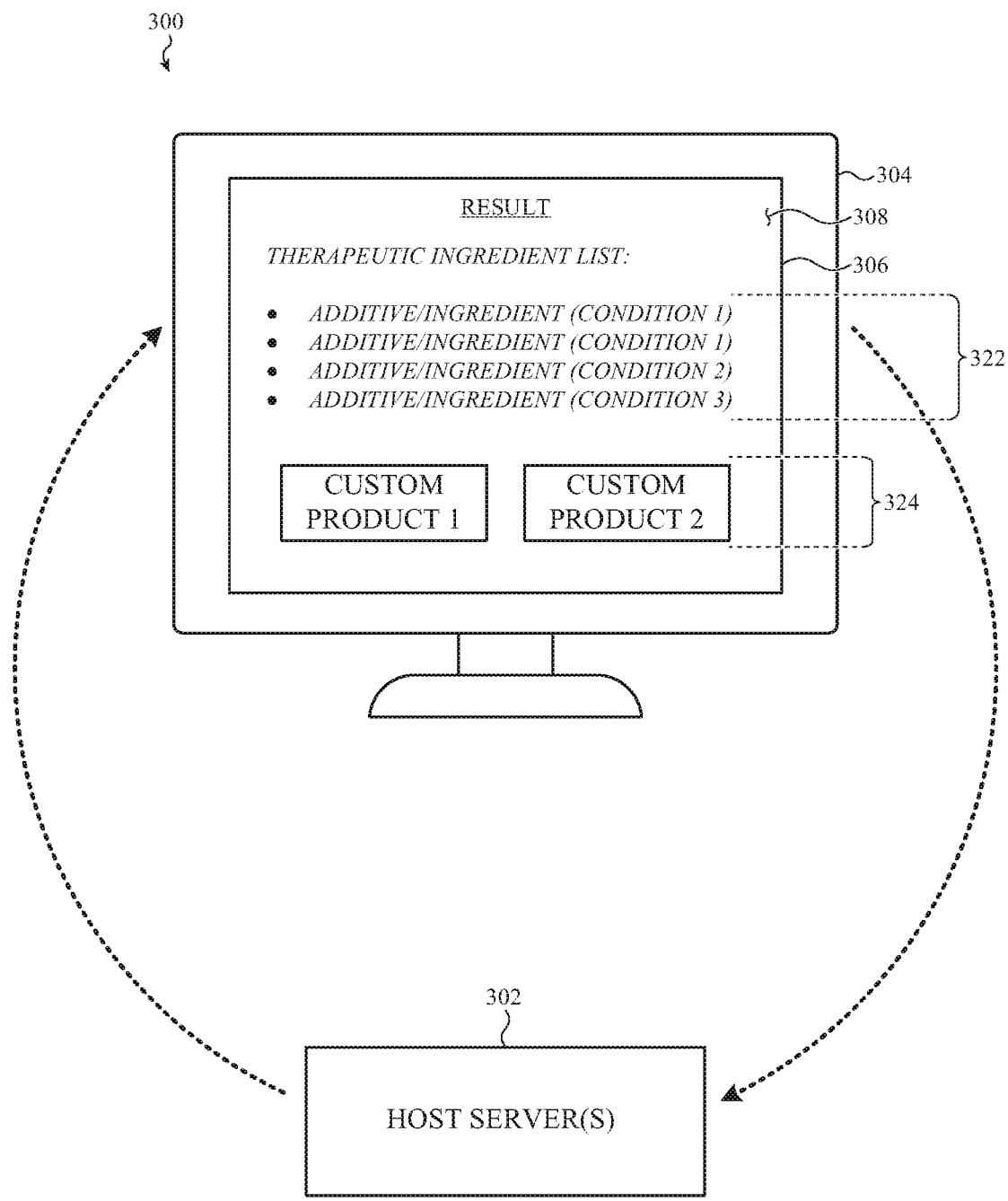
FIG. 3C is a signal/process flow diagram depicting the client device of FIG. 3A rendering a graphical user interface presenting one or more product recommendations to the user of the client device.

In response to generation of one or more prediction matrices, the recommendation engine 302 can be configured to provide one or more recommendations to the user. FIG. 3C is a signal/process flow diagram depicting the client device of FIG. 3A rendering a graphical user interface presenting one or more product recommendations to the user of the client device. In this embodiment, the host server 302 instructs the client device 304 to display, via the display 306 and the graphical user interface 308, a set of recommendations 322 for the user. In some embodiments, the user may be further presented with an option to purchase a customized product by selecting a custom product 324.

Generally and broadly, FIGS. 4-13 depict flowcharts that correspond to various methods of operating a host server, such as described herein, to perform one or more operations of a recommendation engine or service, such as described herein.

As with other embodiments described herein, the embodiments that follow reference an example configuration in which a host server of a recommendation system is configured to provide product and/or ingredient, whether active or inactive, recommendations to a user of a client device in communication with that host server related to skincare and dermatological concerns of the user. In particular, the embodiments that follow contemplate a user presenting with facial skincare concerns, but this is merely one example and other skin concerns, treatments, or interventions may be possible or recommended by a host server configured differently in other embodiments.

Also as with other embodiments described herein, a "user" of the host server referenced by the embodiments that follow is referred to as a "user," however, it may be appreciated that this is merely one example of a user type that can access or leverage a recommendation system described herein. More particularly, it may be appreciated that a recommendation system such as described herein can be suitably configured to provide product or service recommendations based on user demographics, user input (e.g., survey results and the like), product or service attributes, as well as other data sources.

Figure 4:
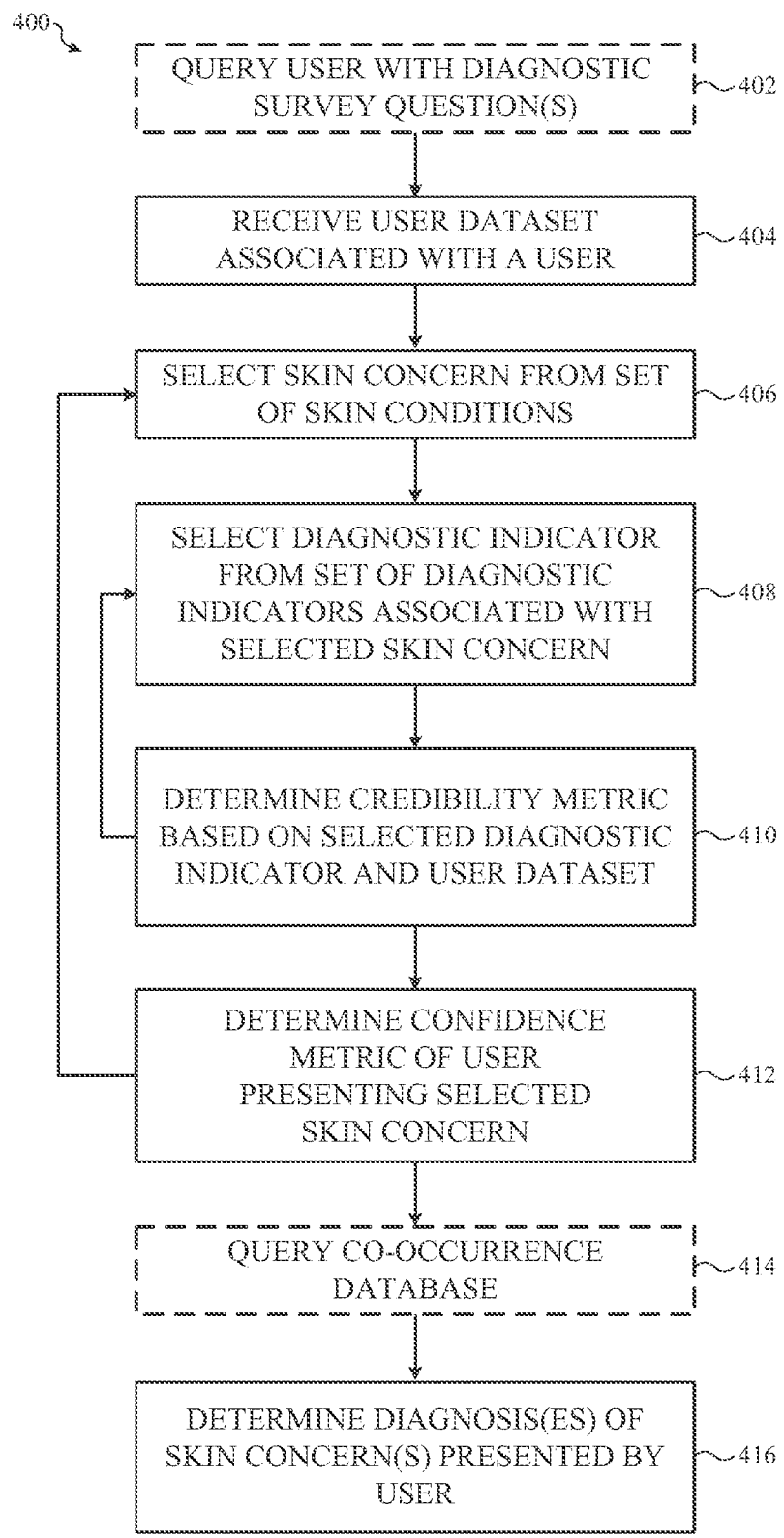
FIG. 4 is a flowchart corresponding to a method of operating a host server to diagnose a user with a skin concern, such as described herein.

FIG. 4 is a flowchart corresponding to a method of operating a host server to diagnose a user with a skin concern, such as described herein. The method 400 can be performed, in whole or in part, by any suitable service, server, processor, or other computational resource allocation associated with a host server, such as described herein. For example, the method 400 can be performed in whole or in part by a host server such as described above in reference to FIGS. 1-3C. In one example, the method 400 can be performed by a server or cluster of communicably coupled servers that are configured to communicate with a client device of a user, such as a cellular phone or a laptop or desktop computer.

The method 400 includes operation 402 (which may be optional in some embodiments), in which the host server serves or otherwise provides a diagnostic survey or questionnaire to the user via the client device. As noted with respect to other embodiments described herein, the diagnostic survey or questionnaire can include any number of suitable questions, taking any suitable form or format, and may be dynamic or static.

For example, in some embodiments, a static questionnaire can be served in a machine-readable format by the host server to the client device. Once the machine-readable format is received by the client device, a processor of the client device can cause a client application executed by that processor to render one or more questions on a display of the client device. The questions of the questionnaire can be presented by the client device in any suitable manner, including but not limited to: presenting one question at a time; presenting related questions together; presenting questions divided into groups; and so on. The questions of the static questionnaire can be any suitable questions that solicit input from the user operating the client device. In these and related embodiments, all users accessing the host server can be served the same questionnaire.

In other embodiments, a static questionnaire served to a client device to solicit input from a particular user by the host server can be selected from a set or group of static questionnaires stored in a database accessible to the host server. For example, a set of static questionnaires may be stored by a database service of the host server, such as described above in reference to FIGS. 1-2.

In these examples, the host server and/or client device can select a single static questionnaire based on one or more characteristics of the user. For example, in some embodiments, the static questionnaire served to a particular user may be based on that user's demographic data (e.g., age, sex, location, preferred language, and so on). In one particular example, a first static questionnaire can be served to male users whereas a second static questionnaire can be served to female users. It may be appreciated, however that this is merely one example; a person of skill in the art will readily appreciate that any suitable number of static questionnaires can be stored by a database service (or other, third-party or first-party storage medium, apparatus, or appliance) of a host server, such as described herein. Examples include static questionnaires selected based on: gender of a user; geographic location of a user; age of a user; age group of a user;

medical condition of a user; allergy of a user; lifestyle of a user (e.g., active, sedentary, and so on); and the like.

In still further embodiments, the method 400 at operation 402 serves or otherwise provides a dynamic diagnostic survey or questionnaire to the user via the client device. In these examples, a dynamic questionnaire may ask questions in an order and with content specific to the user answering those questions. A client device providing a dynamic questionnaire served by the host server can be configured to present follow-up questions, to omit irrelevant questions (as determined by user input, user demographics, and/or answers to previously-presented questions), to ask supplemental questions, and so on. These examples are not exhaustive; a person of skill in the art will readily appreciate that a host server and/or a client device can be configured in any suitable manner to ask questions of a user in a dynamic manner.

For example, in some embodiments, the host server can be configured to transmit the dynamic questionnaire in a machine-readable format to a client device. The client device can parse the machine-readable format of the dynamic questionnaire in order to determine which questions to ask, in which order, and at what time. In these cases, the machine-readable format can encode information related to a variety of "paths" that may be taken by a user through a series or set of questions of the dynamic questionnaire. These paths may change, may fork in different directions, or may terminate based on user input to questions presented to the user.

In other examples, the host server can be configured to transmit questions, individually or in groups, to the client device and the client device can be configured to transmit answers to those questions back to the host server. Upon receiving user input in response to transmitting one or more questions to the client device, the host server can determine which questions to ask of the user next. In some embodiments, the host server can leverage a predictive model, such as described above, in order to determine an order in which to ask specific questions of a specific user (e.g., a user exhibiting or presenting with particular skin concerns, particular demographics and the like).

For example, the predictive model can be trained with user interaction data (e.g., dwell time, click-through rate, and the like) to determine which questions of a given set of questions are more likely to be answered by users than others. In these examples, the predictive model may be configured to determine a statistical likelihood of whether a particular user is likely to answer a given question truthfully, quickly, thoughtfully (e.g., by providing detailed input), or whether that particular user is likely to skip the given question or to exit the dynamic questionnaire altogether. In these embodiments, the predictive model can be leveraged to determine which questions are asked in which order of which user.

For example, the predictive model may determine that a first age bracket (e.g., 30 to 40) is more likely to provide input and/or answer questions of a questionnaire with more than 20 questions, whereas a second age bracket (e.g., 16 to 24) is less likely to provide input and/or answers questions to a questionnaire of that length. In this example, the predictive model may present a shorter dynamic questionnaire to younger users in order to improve click-through and/or completion of the questionnaire for users in that age bracket.

In another example, the predictive model may determine that users indicating a concern with comedones may exhibit an increased click-through or completion rate for longer questionnaires whereas users indicating a concern with dry skin may exhibit a decreased click-through rate or completion rate for longer questionnaires. In this example, the predictive model may present a shorter dynamic questionnaire to users concerned with dry skin and may present a longer dynamic questionnaire to users concerned with comedones in order to improve click-through and/or completion of the questionnaire for users with both concerns.

Regardless the form or format of the questionnaire, whether static or dynamic, it may be appreciated that questions associated with a questionnaire described herein (e.g., served by the method 400 at operation 402) can be presented in any suitable form or format. Example questions, as noted above, can include without limitation: questions answerable by selecting one option among a list of options; questions answerable by providing written, typed, spoken, or otherwise recorded user input; optional questions; required questions; questions answerable by selecting one or more options among a list of options; and so on and the like.

The questions of a questionnaire that can be served by a host server to a client device, such as described herein can include questions soliciting input from the user related to skin concerns such as questions asking whether the user is concerned with: dry, oily, or flaky skin in a particular area; wrinkled skin (e.g., fine lines, deep wrinkles); a skin irritation; loss of firmness or elasticity of skin; skin puffiness; discoloration (e.g., hyperpigmentation, hypopigmentation, vitiligo, melasma, dark spots, sun spots, liver spots, age spots, redness); a perceived skin dullness; blemishes, comedones (closed or open), or scarring; a frequency of a recurring skin concern (e.g., frequency of breakouts, seasonal dryness, and so on); hormonal effects on skin of pregnancy, hormone replacement or supplement therapy, menopause/perimenopause, postpartum; new or worsening skin sensitivity; skin damage (e.g., abrasion, scarring, burning, and the like); a visible appearance of pores; skin texture; visibility of veins; sunken skin or dropping skin; and so on and the like.

The questions of a questionnaire can further include demographic questions such as but not limited to: name; address; ethnicity(ies); age; sex; gender; and so on. In still other examples, the questions of a questionnaire can include medical information such as, but not limited to: allergy information; medication information; dietary information; activity level/lifestyle information; and so on. It may be appreciated that these examples are not exhaustive; a questionnaire such as described herein can solicit any suitable information from a user; the quantity, detail, depth, and type of information or data solicited from a user may vary from embodiment to embodiment.

Once a questionnaire has been completed by the user operating the client device, the method 400 can advance to operation 404 and the client device can communicate or otherwise transmit the input(s) provided by the user back to the host server as a user dataset or, more generally, as user data. In some examples, the client device and/or the host server can normalize one or more fields of the user data. In some examples, the client device and/or the host server can supplement the user data with information retrieved from or queried from a third-party or first-party database. For example, in one embodiment, the client device can be configured to bundle a location of the client device with the user information. In another example, the host server can be configured to access a third-party database, such as a medical database, a medical records database, a genealogy or ancestry database, or the like to supplement the user data with additional data associated with or otherwise linked to the user that completed the questionnaire. These examples are not exhaustive; in other configurations or other embodiments the user data can be supplemented, validated, normalized, or otherwise modified in any suitable manner.

Once the user dataset has been received, the method 400 advances to operation 406 in which the host server accesses a list of possible skin concerns from a database, such as from the database service of the host server described in reference to FIGS. 1-2 above. For each skin concern of the retrieved list, the method 400 can advance to operation 408 at which the host server can query a database of diagnostics associated with the specific skin concern selected at operation 406. A diagnostic may be a sign or a symptom associated with the selected skin concern. For example, if the skin concern selected at operation 406 is rosacea, the set of diagnostics selected at operation 408 may include: redness of the face; swollen blood vessels on nose or cheeks; visible blood vessels; uncharacteristic skin dryness; uncharacteristic skin oiliness; puffy eyes; and so on.

The method 400 at operation 410 can evaluate for each diagnostic a likelihood that the user is actually presenting with that diagnostic. In other words, at operation 410, the host server can calculate or otherwise determine a credibility metric that corresponds to a statistical likelihood that the information and data within the user dataset indicates that the user actually presents the selected diagnostic. For example, the host server (and/or a predictive model thereof) may determine that a higher percentage of users report skin redness in warm geographies. In these examples, the host server (and/or predictive model) may determine a lower credibility metric for skin dermatitis or inflammation-based redness and a higher credibility metric for skin flushing. In another example, the host server may determine that a high percentage of users in a particular demographic, such as younger-aged users, have a tendency to exaggerate or otherwise amplify a sign or symptom experienced by that user. In this example, if a user in a younger age bracket reports extremely dry skin, the host server may determine a neutral credibility metric for dry skin.

In view of the foregoing, in a more general and non-limiting phrasing, the method 400 at operation 410 can determine a likelihood that a sign or a symptom self-reported by the user when responding to the optional questionnaire at operation 402 is likely to be actually presented by that user and whether that diagnostic should be used by the host server when diagnosing the user with one or more skin concerns.

Once a credibility metric has been determined for each, or at least a portion, of the diagnostics of a particular skin concern selected at operation 406, the method 400 can advance to operation 412 in which the method 400 determines a probability, given the user dataset (including demographics and a geographic location of the user, as examples) that diagnosing the user with the selected skin concern would be a correct and true diagnosis. The method can leverage data stored in one or more databases to determine a compound probability that a user with the demographics of the user dataset exhibiting or otherwise presenting with the diagnostics having a credibility metric that exceeds a selected threshold (e.g., greater than 50%, greater than 75%, or another threshold) is correctly diagnosed with the selected skin concern. The method 400 can leverage population occurrence data, user data, the user dataset, and the determinations and calculations made at operations 408 through 410. It may be appreciated that the diagnostic accuracy metric can be calculated in a number of suitable ways.

Once a diagnostic accuracy metric has been calculated or otherwise determined at operation 412, the method 400 can return to operation 406 to select another skin concern with which to advance through operations 410 and 412 again. Once a diagnostic accuracy metric has been calculated for each of the skin concerns identified at operation 406, the method 400 can advance to optional operation 414 at which a skin concern co-occurrence database can be queried to determine which of the skin concerns identified to have a high diagnostic accuracy metric (e.g., exceeding a threshold confidence) are likely to occur together. Similarly, operation 416 can determine whether one or more skin concerns with a high diagnostic accuracy are mutually exclusive. With information retrieved from the skin concern co-occurrence database, the method 400 can optionally filter the set of one or more skin concerns with a high diagnostic accuracy into a set of diagnosed skin concerns that can co-occur. These diagnosis(es) can thereafter be presented to the user. More particularly, the host server can communicate with the client device operated by the user to cause the client device to display a list of the skin concerns diagnosed by the system or server(s) performing the method 400.

It may be appreciated that the foregoing example embodiment is merely one example. In other embodiments, iterative determination of credibility metrics may not be required. For example, in some embodiments, a predictive model, such as the diagnostic predictive model described above with reference to FIG. 2, may be used. More specifically, a host server, such as described herein, may be configured to communicate the user data and/or other data such as geographic data or demographic data, to a predictive model so that the predictive model can ingest that data and output a value that corresponds to a statistical likelihood that a particular user presents with a particular skin concern, or a particular co-occurring set of skin concerns.

Figure 5:
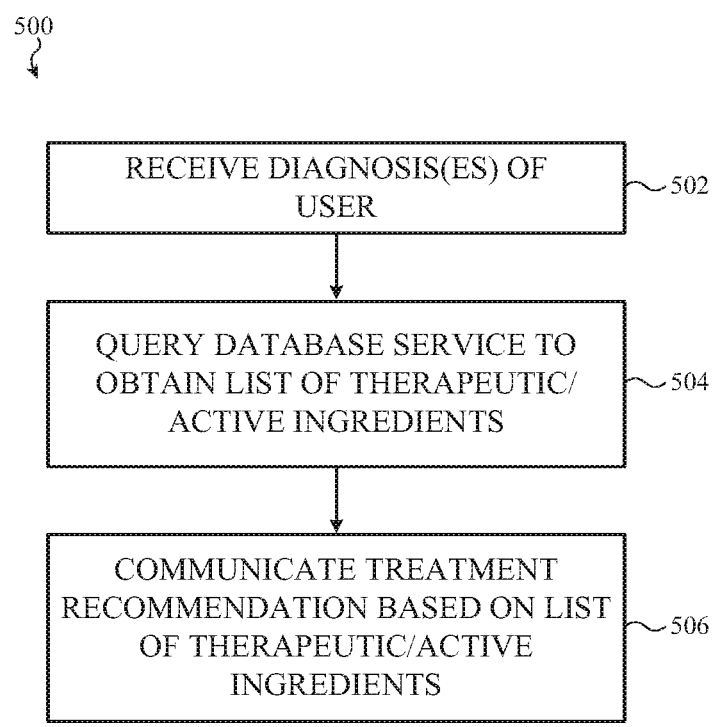
FIG. 5 is a flowchart corresponding to a method of operating a host server to recommend a treatment to a user presenting with, or otherwise exhibiting, a skin concern, such as described herein.

FIG. 5 is a flowchart corresponding to a method of operating a host server to recommend a treatment to a user presenting with, or otherwise exhibiting, a skin concern, such as described herein. As with method 400, the method 500 can be performed, in whole or in part, by any suitable service, server, processor, or other computational resource allocation associated with a host server, such as described herein. For example, the method 500 can be performed in whole or in part by a host server such as described above in reference to FIGS. 1-3. In one example, the method 500 can be performed by a server or cluster of communicably coupled servers that are configured to communicate with a client device of a user, such as a cellular phone or a laptop or desktop computer.

The method 500 includes operation 502 in which a diagnosis of a skin concern of a particular user is received. As noted above, the diagnosis can be determined in a number of suitable ways including, but not limited to: iteratively determining a likelihood that each of a set of diagnostics associated with a given skincare condition is presented and/or exhibited by the user; determining with a predictive model or other suitable artificially intelligent data structure, algorithm, instantiated virtual machine, class, or method a likelihood that a given user is presenting with a particular skincare condition (more simply, determining a likelihood of a diagnosis of a particular skin concern); determining with a predictive model other suitable artificially intelligent data structure, algorithm, instantiated virtual machine, class, or method a skincare condition presented by a given user (more simply, determining a diagnosis of a skin concern from user data); and so on and the like.

Similarly, it may be appreciated that a diagnosis of a user may be received at operation 502 in any suitable form or format. For example, in many embodiments, the diagnosis, which can include an indication of or an indicator associated with one or more skincare conditions presented by a given user, can be transmitted in a machine-readable format such as a diagnostic matrix to a host server, such as described herein. In other cases, a first service of the host server (e.g., a predictive model service) can communicate the diagnosis or data associated therewith to a second service of the same host server.

Independent of the method, form, or format by which the diagnostic data, diagnostic dataset, or diagnostic matrix is received at operation 502, the method 500 can advance to operation 504 at which a database service of a host server, such as described herein, can be queried to determine a set of ingredients, which can include both active ingredients and inactive ingredients that may be therapeutic or otherwise beneficial to one or more of the skin concerns included in or referenced by the diagnostic data. In other cases, the database service can return one or more ingredients based on a user dataset. For example, a user may respond to a questionnaire (see, e.g., FIG. 4) by indicating a preference for or a preference against a particular ingredient, a particular ingredient class (e.g., perfumes, colorants, emulsifiers, acids, bases, emollients, exfoliants, and so on), a particular ingredient source (e.g., organic, non-organic, country of origin, supplier, and so on), a particular ingredient environmental impact (e.g., made from recyclable materials, made with a low carbon footprint, and so on), and so on. For example, the user may indicate a preference against ingredients with an aroma or odor. In another example, the user may indicate a preference for blue or pink dyes. In other example, the user may indicate that the user has an allergy to one or more of glycolic, lactic, mandelic, citric and salicylic acid. In these examples, the method 500 at operation 504 may filter, supplement, or otherwise modify an output of the database service based on one or more user preferences or one or more data items of user data.

The method 500 thereafter advances to operation 506 at which the list of active and/or inactive ingredients, that may correspond to or otherwise be filtered based on a communicated preference of the user, can be communicated as a treatment recommendation to the user and/or to another service of the host server.

For example, in some embodiments, the method 500 can be configured to perform operation 506 by communicating a machine-readable format listing of a set of active ingredients and a set of inactive ingredients, each of which may be filtered by or otherwise informed by user data (optionally), such as described above, to a client device communicably coupled to a host server, such as described herein. The client device, executing a client application rendering a graphical user interface to present information to the user, can be configured to display in any suitable form or format the ingredient list to the user. In some examples, the client application and/or client device can be configured to display an active ingredient list separate from an inactive ingredient list in order to visually emphasize and/or distinguish between active ingredients and inactive ingredients.

In addition, in some embodiments, the system can be configured to, at operation 506, display one or more ingredients, whether active or inactive, that were excluded from the list of ingredients displayed to the user. In other words, the client device and/or the client application can be configured to display ingredients that the user should avoid because the user may be allergic to the ingredient, the ingredient may exhibit an interaction with another ingredient, the ingredient may exhibit an interaction with a medication taken by the user, the ingredient may produce or may be associated with an odor, aroma, color, or texture that is not preferred by the user, and so on.

In still further embodiments, the system and/or method 500 can be configured to, at operation 506, display one or more ingredients that the user should avoid. For example, if the system and/or method 500 determines that the user exhibits a skin concern that would be exacerbated or otherwise advanced by an ingredient, the system can display a recommendation to the user to avoid that ingredient due to a possible negative effect.

In still further embodiments, the system and/or method 500 can be configured to, at operation 506, display one or more ingredients that the user may currently be using that the user may be allergic to and/or that may be triggering one or more skin concerns presented by the user. For example, the method 500 may determine at operation 502 that the user is diagnosed with red skin, sensitive skin, and/or skin dermatitis. At operation 504, the method 500 may additionally query the database service to determine a list of active ingredients that may be associated with one or more of the skin concerns identified at operation 502. For example, the method 500 may determine at operation 504 that formaldehyde can trigger one or more of the identified skin concerns of red skin, sensitive skin, and/or skin dermatitis. In this example, the method 500 at operation 506 may present a recommendation to the user to avoid products containing formaldehyde.

It may be appreciated that the foregoing example embodiments are merely examples and are not exhaustive. In other embodiments, querying a database to obtain the list(s) of therapeutic or otherwise beneficial active ingredients, inactive ingredients, or counter-indicated ingredients may not be required. For example, in some embodiments, a predictive model, such as the diagnostic predictive model described above with reference to FIG. 2, may be used. More specifically, a host server, such as described herein, may be configured to communicate the diagnosis data received at operation 502 along with user data and/or other data such as geographic data or demographic data, to a predictive model so that the predictive model can ingest that data and output a value that corresponds to a statistical likelihood that a particular ingredient will be associated with a positive result for a particular user.

Figure 6:
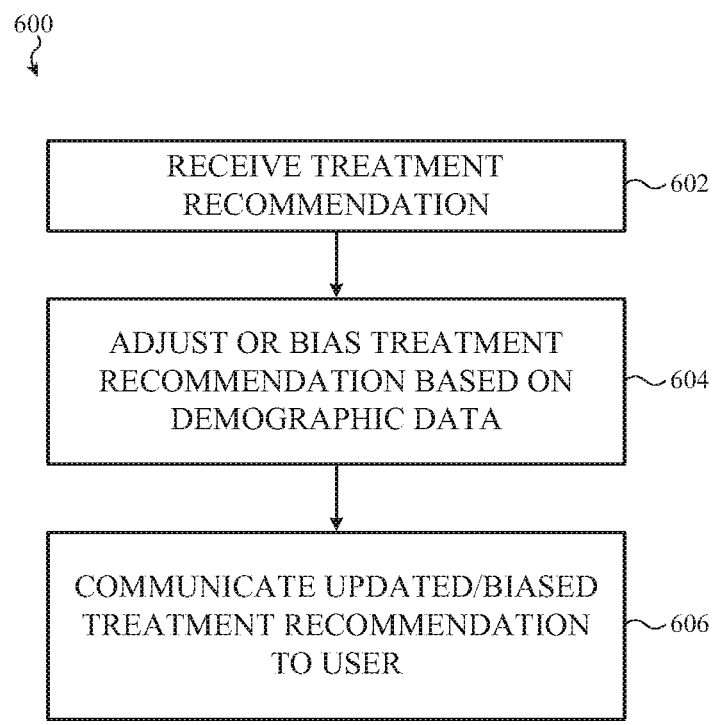
FIG. 6 is a flowchart corresponding to a method of operating a host server to adjust or modify a treatment recommended to a user presenting with, or otherwise exhibiting, a skin concern, such as described herein.

For example, FIG. 6 is a flowchart corresponding to a method of operating a host server to adjust or modify a treatment recommended to a user presenting with, or otherwise exhibiting, a skin concern, such as described herein. As with the methods 400 and 500 described above, the method 600 can be performed by any suitable hardware, software, or combination thereof. This description is not repeated.

The method 600 begins at operation 602 at which a treatment recommendation is received. The treatment recommendation received at operation 602 can include a list of active ingredients, a list of inactive ingredients, a list of user or customer preferences, and so on. In some examples, the treatment recommendation is received by a service provided by a host server such as described herein. In some examples, the treatment recommendation includes information related to a description (e.g., an ingredient source, an ingredient type or class, an ingredient purity, and so on) and/or an intended use (e.g., an ingredient function, a skin concern for which the ingredient is therapeutic or otherwise beneficial, a user preference met by the ingredient, and so on) or purpose of one or more of the ingredients.

In other embodiments, the treatment recommendation also includes information related to a product that incorporates one or more of the ingredients. For example, in some embodiments, a system such as described herein can be configured to access a database, such as the database service described in reference to FIG. 2, to determine whether a product among a list of products that contains a threshold number of ingredients that are therapeutic or otherwise beneficial meets the requirements of a user (e.g., user preferences, user skin concerns, and so on). In these examples, the method 600 at operation 602 can be configured to receive, in addition to or in place of the ingredient list, a product list containing information identifying at least one first- or third-party product recommended for the user. In some cases, the product can be a custom product, such as described herein, in which a selected skincare base is supplemented with one or more additives to create a custom product therapeutic or otherwise beneficial to and/or responsive to the needs or preferences of a particular or given user.

In some examples, the treatment recommendation can further include regimen information, such as information suggesting to the user a product or ingredient and a pattern of use for that product or ingredient.

In still further examples, the treatment recommendation can include a set of custom, over-the-counter, prescription products and, additionally, regimen information suggesting to the user a pattern of use for the set of products.

The method 600 advances to operation 604 at which the treatment recommendation received at operation 602 is adjusted based on demographic data of the user. For example, the method 600 can change a moisture content of a product or ingredient of the treatment recommendation if the demographic data of the user indicates that the user lives in a geography with high humidity. More simply, and without limitation, the method 600 at operation 604 can adjust treatment recommendations and/or recipes based on, in one example, local humidity averages.

In another example, the method 600 can change a sun protection factor (e.g., can change an ingredient with a different sun protection factor) of a product of the treatment recommendation if the demographic data of the user indicates that the user lives in a geography with high altitude. More simply, and without limitation, the method 600 at operation 604 can adjust treatment recommendations and/or recipes based on, in one example, local ultraviolet indices, local weather predictions, local altitude, and the like.

In yet another example, the method 600 can substitute a first active or inactive ingredient for a second, different, active or inactive ingredient (e.g., the first ingredient having an equivalent therapeutic or otherwise beneficial, aesthetic, or fragrance effect as the second ingredient) of a product of the treatment recommendation if the demographic data of the user indicates that the user has a preference for the second ingredient or, additionally or alternatively, has a preference against the first ingredient. More simply, and without limitation, the method 600 at operation 604 can adjust treatment recommendations and/or recipes based on, in one example, user preferences.

The foregoing examples are not exhaustive; a person of skill in the art will appreciate that any number of suitable modifications, adjustments, or biases can be applied to a treatment recommendation, or a portion thereof (e.g., regimen, ingredient list, additive list, skincare based, and so on), in response to any suitable trigger, signal, or other indication. Example data that can influence a change to a treatment recommendation such as described herein can include, but is not limited to: local weather predictions; local pollution estimations; local air quality index; local water hardness data; local water additive data (e.g., fluoride, chlorine, chloramine, and the like); time of year information; user travel plans/information (e.g., temporarily or permanently moving from one geography to another geography); local season; user allergy information; user medical information; user preference information; cost of an ingredient; source of an ingredient (e.g., organic, nonorganic, sustainable source, and so on); environmental impact of an ingredient; and the like and so on.

Thereafter, the method 600 advances to operation 606 at which the modified, adjusted, changed, or otherwise altered treatment recommendation is communicated to the user. As with other embodiments described here, the updated treatment recommendation can be packaged in a machine-readable format by a host server, such as described herein, and can be thereafter transmitted across a suitable communication channel (e.g., wired, wireless, the open Internet, and so on), to a client device operated by the user for whom the treatment recommendation is intended. The client device can thereafter display all or part of the treatment recommendation to the user via a display of the client device.

In still other examples, a predictive model may be used to inform treatment recommendation adjustments, such as described above. For example, a predictive mode (see, e.g., FIGS. 1-2) can be configured to ingest user data, diagnostic data, and/or other data in order to determine a user-specific treatment for one or more skin concerns presented by that user. In many of these embodiments and examples, a predictive model may be configured to generate a statistical value that corresponds to a statistical likelihood that a given user (defined, for the system, as a given user dataset) will have a positive treatment experience when using a particular product or combination of ingredients according to a given treatment recommendation. More simply, and without limitation, the predictive model can be configured to generate a metric that represents a prediction of whether a user will leave a positive product review.

Figure 7:
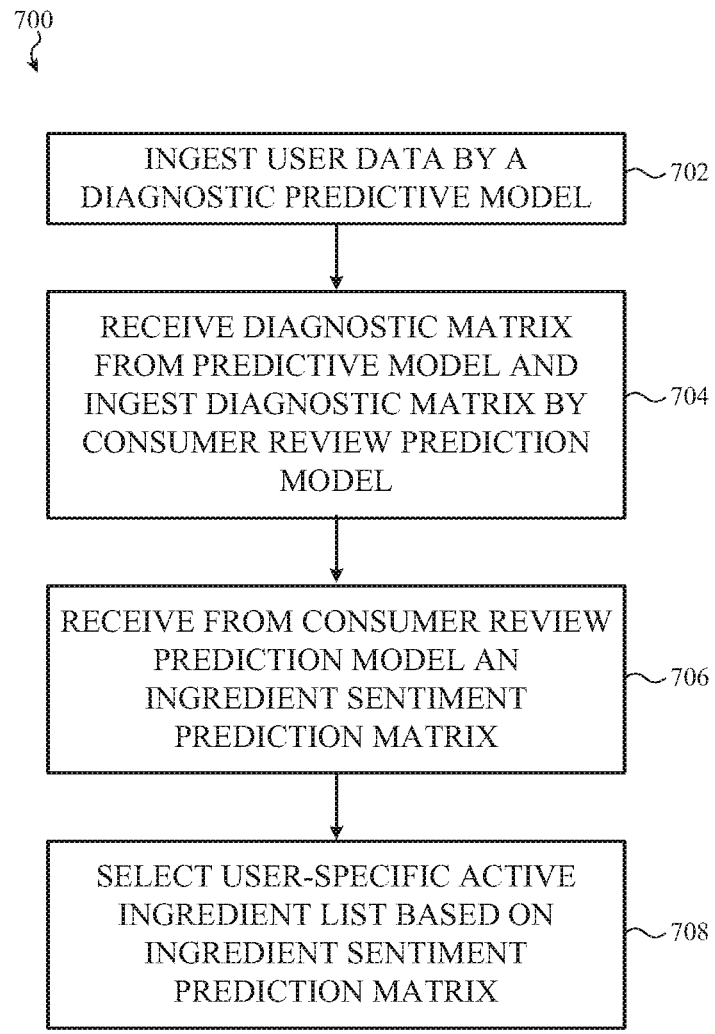
FIG. 7 is a flowchart corresponding to a method of operating a host server to determine a set or list of active and/or inactive ingredients likely to elicit a positive review from a user if used by that user to treat a skin concern, such as described herein.

For example, FIG. 7 is a flowchart corresponding to a method of operating a host server to determine a set or list of active and/or inactive ingredients likely to elicit a positive review from a user if used by that user to treat a skin concern, such as described herein. As with other methods described herein, the method 700 can be performed in whole or in part by any suitable software or hardware or combination thereof, such as described above in reference to methods 400-600. This description is not repeated.

The method 700 includes operation 702 at which a predictive model ingests user data. In this example, the predictive model can be referred to as a diagnostic predictive model at least in part because an output of the diagnostic predictive model corresponds to a prediction of whether the user presents with a particular skin concern.

More particularly, at operation 704, the method 700 advances to receive a diagnostic matrix from the diagnostic predictive model. The diagnostic matrix can be defined as a data structure having entries, each of which corresponds to a statistical likelihood that the user exhibits a particular skin concern associated with that respective entry. In this manner, in a more simple and non-limiting phrasing, the diagnostic matrix can be a collection of predictions or a collection of diagnostic probabilities in which (1) a low probability corresponds to a determination by the diagnostic predictive model that the user does not present with the associated or respective skin concern, (2) in which a high probability corresponds to a determination by the diagnostic predictive model that the user does present with the associated or respective skin concern, and (3) in which a neutral probability between a low probability and a high probably corresponds to a determination by the diagnostic predictive model that the user may or may not present with the associated skin concern; there is not enough information for the model to affirmatively diagnose the user with the skin concern nor is there enough information for the model to affirmatively exclude a possibility that the user presents with the skin concern.

Additionally, at operation 704, the method 700 is configured to leverage a second predictive model, referred to herein as a consumer review prediction model, to obtain a prediction of whether a particular ingredient or treatment is likely to elicit a positive customer review from the user. To that end, at operation 704, the method 700 ingests the user data and/or the diagnostic matrix by the consumer review prediction model to determine a set of active and/or inactive ingredients that would likely elicit a positive review from the user. In another phrasing, the model ingests the user data and/or the diagnostic data to determine which sets of ingredients can be combined, in which quantities, and/or in which products or product types in a manner that is responsive to all of the likely skin concerns presented by the user (e.g., as determined by the diagnostic predictive model at operation 702). More simply, the model at operation 704 lists ingredients that are likely to be therapeutic or otherwise beneficial enough to the user that the user would notice a positive improvement in one or more of the skin concerns experienced by the user. Similar to the diagnostic predictive matrix, the consumer review predictive matrix can be configured to output a matrix, referred to herein as an ingredient sentiment prediction matrix, that can be leveraged by the method 700 for additional purposes. More particularly, at operation 706 the method 700 receives from the consumer review prediction model an ingredient sentiment prediction matrix, the entries of which correspond to prediction(s) that a particular ingredient would likely elicit a positive review from the user.

Thereafter, the method 700 advances to operation 708. At operation 708, the method 700 can select from the ingredient sentiment prediction matrix a set of ingredients that when used in combination and according to a particular regimen are likely to elicit a positive review from the user.

Figure 8:
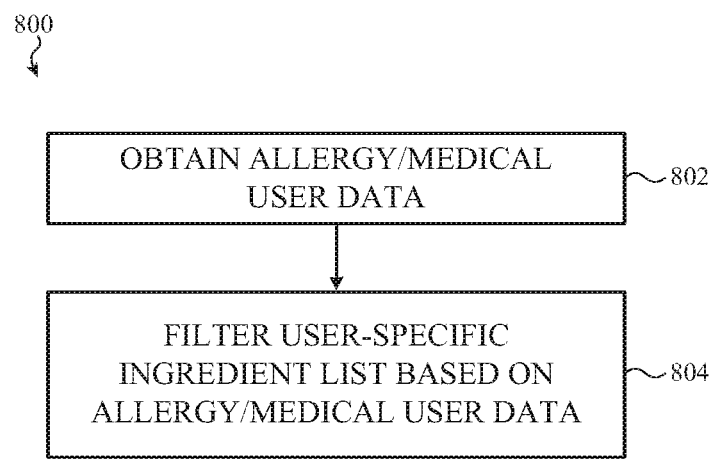
FIG. 8 is a flowchart corresponding to a method of operating a host server to filter a set or list of active and/or inactive ingredients based on user allergy or medical information or data, such as described herein.

In still other examples, a user-specific ingredient list can be determined in another manner. For example, FIG. 8 is a flowchart corresponding to a method 800 of operating a host server to filter a set or list of active and/or inactive ingredients based on user allergy or medical information or data, such as described herein. As with other method embodiments described herein, the method 800 can be performed in whole or in part by any suitable combination of hardware, software, processors, circuits and the like.

The method 800 begins at operation 802 at which user data is obtained. In particular, in this embodiment, the user data includes at least allergy information and/or medical information. Example allergy information that can be included with the user data can include, without limitation: food allergy information; particle allergy information (e.g., pollen, dust mites, mold, animal dander, and the like); venom allergy information (e.g., insect stings, and the like); medicine allergies; and the like. Example medical information that can be included with the user data can include, without limitation: over-the-counter medicine taken by the user; prescription medicine taken by the user; and so on.

Thereafter, the method 800 advances to 804 at which a user specific ingredient list can be filtered based on the user data received at operation 802.

Figure 9:
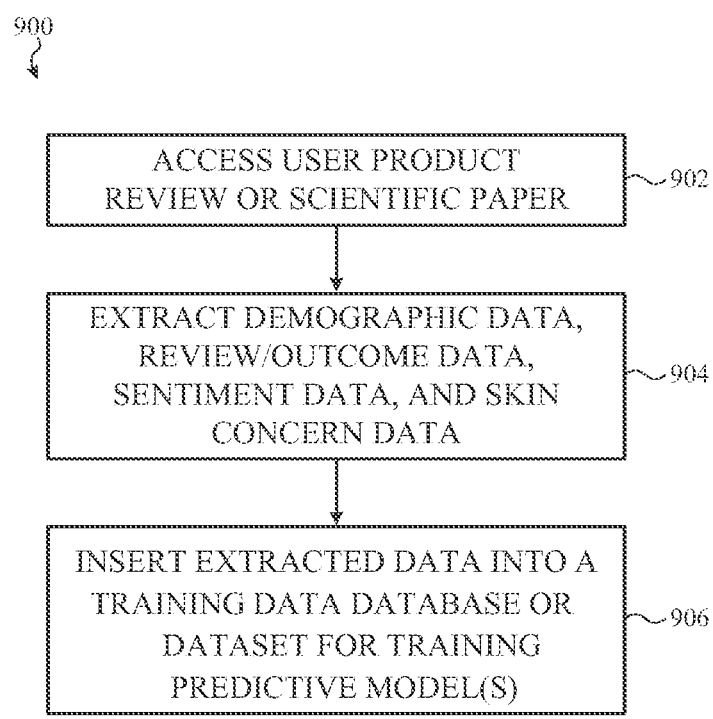
FIG. 9 is a flowchart corresponding to a method of operating a host server to generate training data for training a predictive model, such as described herein.

FIG. 9 is a flowchart corresponding to a method of operating a host server to generate training data for training a predictive model, such as described herein. The method 900 includes operation 902 at which customer review data and/or scientific research data is accessed, collectively referred to as "source" data. The source data can be obtained from any suitable first-party database (e.g., the database service, such as described above) or any suitable third-party database.

In many examples, the source data is accessed via the open Internet from a publicly-accessible database. For example, the source data can be hypertext markup language or javascript object notation formatted data obtained from a third-party website.

Thereafter, at operation 904, the method 900 advances to extract demographic data of the author of the source data, review content data (e.g., title, body, ranking on a graduated scale, and the like), sentiment data (e.g., positive sentiment, negative sentiment, or neutral sentiment), and skin concern or diagnostic data. Each of these and/or other data items extracted from the source data can be extracted in any suitable form or format and may be normalized, supplemented, processed, or otherwise modified in any suitable manner.

In some examples, demographic data corresponds to the individual who authored the customer review or, in the case of a scientific paper, the subject of a study referenced in the scientific paper. Demographic data extracted from the source data (and/or another source, such as a customer profile page) can include, without limitation: gender; ethnicity; age; geographic location; a time of year at which the source review was left and/or the source scientific study was conducted; and the like.

Review content data extracted from the source data can include, without limitation: a product that is a subject of the review; a manufacturer that is a subject of the review; a ranking or other quantization of the positivity of the customer's experience (e.g., a graduated scale, such as 1 through 5 stars); a review title; a review body; review tags; a number of comments to the review; a number of times the review has been cross-linked, shared, liked or otherwise interacted with by others; a keyword associated with the review; whether the author of the review followed up at a later time to amend the review; and so on and the like. In many examples, the review content data further includes ingredient information obtained from a third-party database. More specifically, for each product referenced in the review (or scientific paper), the method 900 can be configured to obtain an ingredient list for that product. As with other embodiments described here, the method 900 can be configured to separate active ingredients and inactive ingredients and can be configured to estimate an approximate proportion and/or quantity by volume of each ingredient or at least a subset of ingredients.

Sentiment analysis can be performed in any suitable manner according to any suitable sentiment analysis technique. Sentiment data extracted from the source data can include, without limitation: positive sentiment words or phrases; negative sentiments words or phrases; overall review content sentiment; sentiment of responses to the review (e.g., responses by a manufacturer, and so on).

Skin concern and/or diagnosis data extracted from the source data (and/or another source, such as a customer profile page) can include, without limitation: colloquial phrasing associated with one or more user symptoms or signs; medical phrasing associated with one or more user symptoms; and the like; phrasing associated with a result or outcome; phrasing associated with a later-developed sign or symptom; phrasing indicating a recommendation of a doctor, dermatologist, or other medical resource; and so on. In many examples, skin concern and/or diagnosis data can be similar to and/or associated with one or more diagnostics such as described above (see, e.g., FIG. 4).

Thereafter, at operation 906, the method 900 advances to insert the extracted data into a training data database. Once a new row (or multiple rows in one or more tables or organized in a different manner) is inserted into the training data database, a re-training and/or a training operation can be triggered such that a predictive model, such as described herein can be trained in view of the newly-extracted data.

It may be appreciated that that the foregoing example embodiments are not exhaustive of the ways in which a host server or service, such as described herein, can be operated. In particular, the foregoing example embodiments referencing one or more predictive models leveraged by example host servers can be used and/or trained in different manners than those described above. More generally and broadly, it may be appreciated that the foregoing embodiments reference a system in which user data, some of which may be self-reported by the user, can be consumed by a predictive model to obtain a set of likely skin concerns exhibited by that user. Thereafter, another predictive model can consume the prediction of the first predictive model and the user data in order to determine a listing of combinable and/or non-interactive appropriate ingredients that can be used by the user to treat the diagnosed skin concerns. As with other embodiments described herein, this can be referred to as a "user-specific ingredient list."

With this data, the host server can perform a number of functions and/or can provide a number of recommendations to the user associated with the user data. For example, if the user supplies a list of skincare products currently being used by the user, the host server can compare the ingredients in the products identified by the user and can compare ingredients of those products to the user-specific ingredient list. Therewith, the host server can make one or more recommendations based on the current products used by the user, for example, the system may recommend that the user replace a first product with another product, may inform the user that a first product exhibits interactions with a second product, may recommend to the user to stop using a product altogether, and so on.

In other cases, the system can be configured to use the user-specific ingredient list to recommend to the user products available for purchase at a retail store nearby a geographic location of the user. In still other cases, the system can be configured to use the user-specific ingredient list to recommend to the user to use a particular line of products produced by a particular manufacturer. In other cases, the user-specific ingredient list can be used by the system to inform the user of a likely or probable allergy detected by the system. It may be appreciated that these foregoing examples are not exhaustive; a user-specific ingredient list can be leveraged by a system such as described herein for any suitable purpose or combination of purposes.

Figure 10:
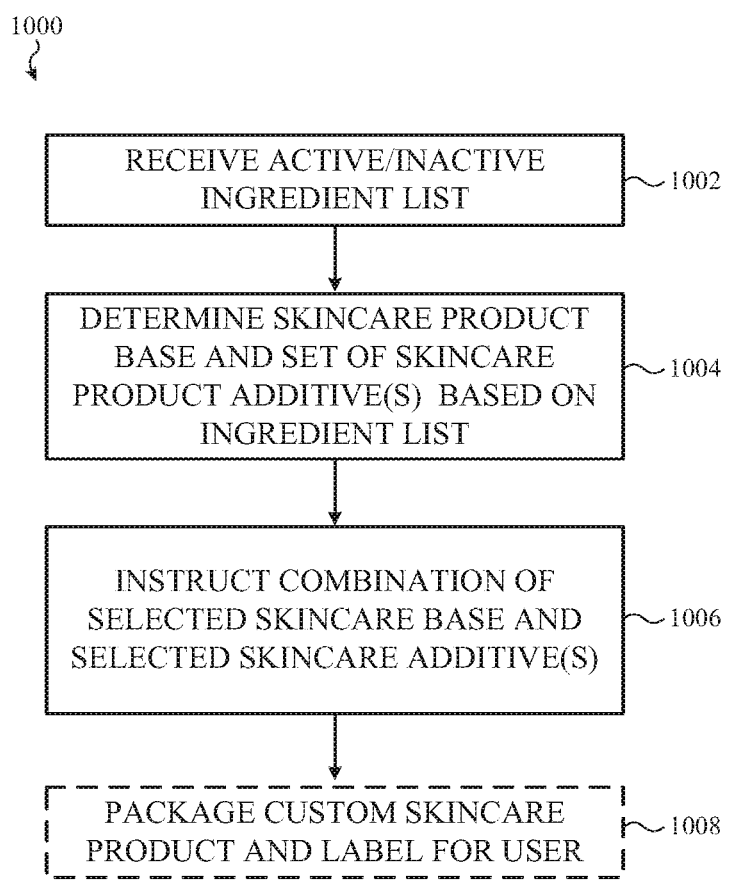
FIG. 10 is a flowchart corresponding to a method of on-demand manufacturing of a custom skincare product, such as described herein.

In certain further embodiments, a user-specific ingredient list such as described herein can be used to produce a user-specific skincare product. In particular, FIG. 10 is a flowchart corresponding to a method 1000 of on-demand manufacturing of a custom skincare product, such as described herein.

The method 1000 includes operation 1002 at which a user-specific ingredient list is received. Next, at operation 1004, a skincare product base (also referred to as a bulk base) can be selected from a set of skincare product bases. The skincare product base may be selected based on a determined match between ingredients of the selected product base and the user-specific ingredient list.

In addition, at operation 1004, one or more skincare product additives can be selected from a set of skincare product additives. The skincare product additives can be mixtures of ingredients, separate ingredients, or any other suitable additive (e.g., abrasives, textures, colorants, perfumes, and so on and the like). As with the skincare product base, the skincare product additives may be selected based on a determined match between ingredients of the selected product additive(s) and the user-specific ingredient list.

One of skill in the art may appreciate that as a result of separating additives and bases, arbitrarily large number of products can be customized on a per-user basis without requiring mass manufacture of individual SKUs. For example, in one implementation, a system such as described herein has access to 10 separate skincare bases and 30 skincare additives. In this example, if a skincare product can have up to 10 additives per base, many possible combinations exist (e.g., hundreds of millions of combinations).

Thereafter, at operation 1006, the method 1000 advances to instruct a manufacturing mechanism to combine the selected skincare base and the selected skincare additives to manufacture a user-specific, custom product. Optionally, the method 1000 can advance to operation 1008 at which the custom skincare product manufactured at operation 1006 can be packaged in a manner custom to the user. For example, a packing of the custom skincare product can be printed with the user's name, with a user photo, with a custom color scheme selected by the user, and so on. It may be appreciated that these isolated examples are not exhaustive and that a custom skincare product can be customized in any suitable manner.

Figure 11:
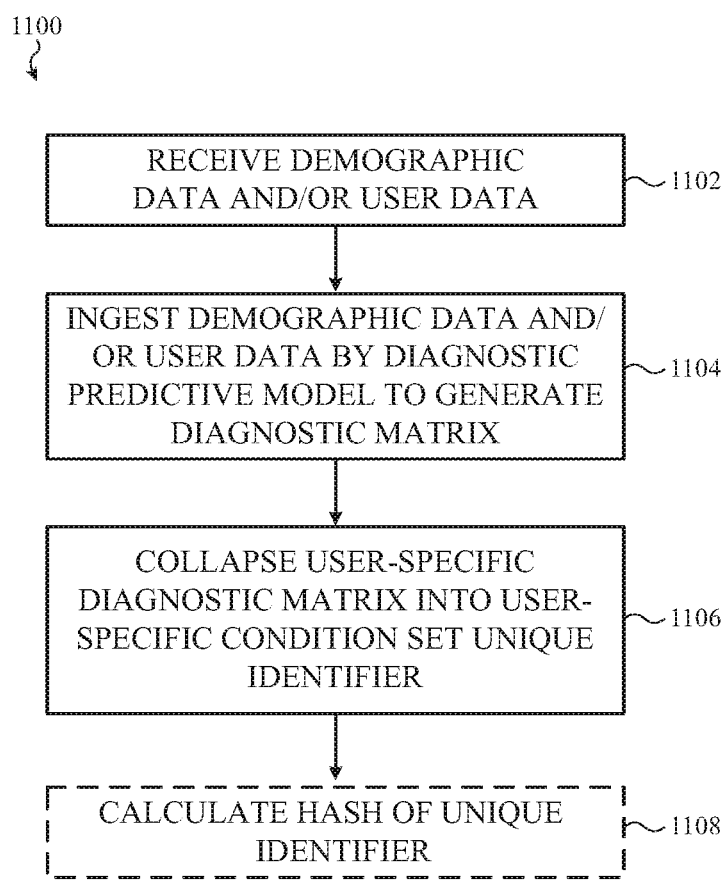
FIG. 11 is a flowchart corresponding to a method of operating a host server to generate a user-specific unique identifier corresponding to skin concern(s) and/or demographic data unique to that user, such as described herein.

In many cases, a user such as described herein may be motivated to order a custom skincare product again. As such, in many embodiments, a system such as described herein can be configured to generate a user-specific identifier that corresponds to a particular user and a particular set of skincare conditions exhibited by that user at a particular time. For example, FIG. 11 is a flowchart corresponding to a method 1100 of operating a host server to generate a user-specific unique identifier corresponding to skin concern(s) and/or demographic data unique to that user, such as described herein. The method 1100 includes operation 1102 in which demographic data and/or other user data can be received. Next, at operation 1104, the received data can be ingested by a predictive model to generating a diagnostic matrix, such as described above. Next, at operation 1106, the user-specific diagnostic matrix can be collapsed into a single scalar or string value or a single vector (e.g., a set of user-specific values corresponding to entries in the diagnostic matrix). Thereafter, optionally, at operation 1108, a hash of the collapsed/flattened value obtained at operation 1006 can be calculated and stored in a database. In this manner, the system can readily access user diagnostic data and/or user ingredient data for future purchases of custom skincare products.

Figure 12:
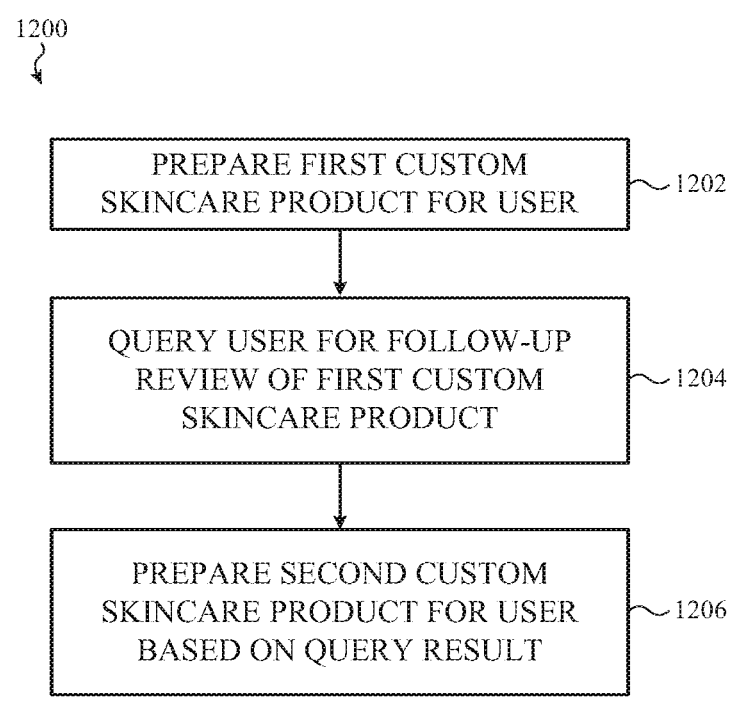
FIG. 12 is a flowchart corresponding to another method of on-demand manufacturing of a custom skincare product, such as described herein.

In some examples, a user-specific skincare condition set identifier can be used to track a user history over time. For example, FIG. 12 is a flowchart corresponding to another method 1200 of on-demand manufacturing of a custom skincare product, such as described herein. In this example embodiment, the method 1200 begins at operation 1202 at which a first custom skincare product is prepared for a given user. Next, at operation 1204, after at least a threshold period of time has passed, the system can query the user for feedback on how well or poorly the custom product addressed the skin concerns of the user. Based on this feedback, at operation 1206, the method 1200 can retrain one or more predictive models and/or can prepare a second, updated, custom skincare product for the user.

Figure 13:
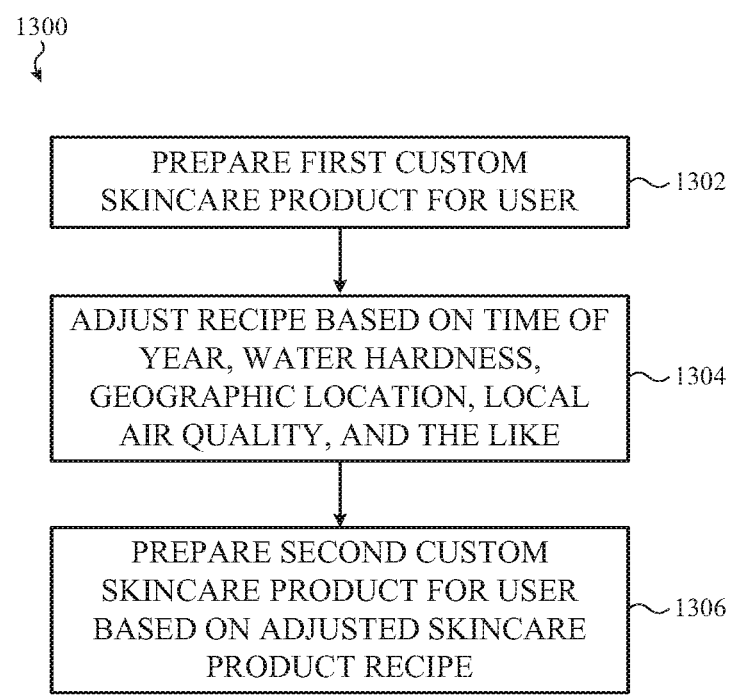
FIG. 13 is a flowchart corresponding to another method of on-demand manufacturing of a custom skincare product, such as described herein.

FIG. 13 is a flowchart corresponding to another method of on-demand manufacturing of a custom skincare product, such as described herein. In this embodiment, the method 1300 begins at operation 1302 at which a first custom skincare product is prepared for a given user. Next, at operation 1304, one or more ingredients of that product can be adjusted based on one or more conditions of use of that product. For example, user demographic data can inform the method 1300 that the user lives in a geography with hard water. This determination can be leveraged by the method 1300 at operation 1304 to change the first skincare product recipe based on the water hardness of the location at which the user is likely to use the product. Other data that may inform the method 1300 at operation 1304 include, but are not limited to: time of year and/or season; location-specific weather predictions; location-specific water hardness; location-specific air quality; and so on.

In further examples, the method 1300 can be leveraged by a user to receive a custom skincare product for travel purposes. In other words, a user can inform the system implementing the method 1300 that the user intends to travel for a period of time to another location. With this information, the method 1300 at operation 1306 can adjust one or more characteristics of a product or recipe used to manufacture a custom product for that user based on, among other things, (1) a duration through which the user will stay in the identified location (e.g., how long a vacation is planned to be), and (2) geographic and/or other local data specific to the target location.

It is understood that the foregoing and following descriptions of specific embodiments are presented for the limited purposes of illustration and description. These descriptions are not targeted to be exhaustive or to limit the disclosure to the precise forms recited herein. To the contrary, it will be apparent to one of ordinary skill in the art that many modifications and variations are possible in view of the above teachings.

For example, although many embodiments described herein leverage output(s) of one or more predictive models that consume user geographic and/or demographic data to inform production of a customized or custom-tailored skincare product (e.g., by combining a skincare base and one or more skincare additives), this is not required of all embodiments. For example, it may be appreciated that any suitable embodiment described herein can be modified to leverage output of a predictive model to select and recommend to a user one or more skincare products from a set of skincare products. In these examples, a host server and/or a predictive model of the host server can be configured to select the one or more skincare products based on a quantity of active and/or inactive/cosmetic ingredients contained in those products that match with active and inactive ingredients output from the predictive model. In other cases, one or more skincare products can be selected from a set of skincare products based on one or more active ingredients of the selected skincare products that are determined by the predictive model to be of greater therapeutic and/or otherwise beneficial use to the user. These examples are not exhaustive; it is appreciated that any suitable embodiment described herein, along with equivalents thereof, can be suitably modified to, without limitation: recommend existing products; generate custom products; recommend routine changes; recommend a user stop using a specified product or ingredient; recommend the user consult a dermatologist or aesthetician; recommend the user adopt a particular skincare routine; recommend the user adjust the user's diet; recommend the user purchase a water filter for the user's primary residence; recommend the user wear or avoid wearing particular clothing or jewelry; recommend the user change detergents; soaps or other products used by the user; and so on or any combination thereof.

For example, as noted above, although the embodiments presented herein reference methods of leveraging predictive models trained by scraping customer review data, scientific data, and other data sources to generate a diagnosis of a skin concern and, additionally, product and, more specifically, product attribute (e.g., ingredients) recommendations to a user exhibiting those skin concerns, it may be appreciated that this is merely one implementation and configuration and use of a system described herein.

In other cases, a system such as described herein can be trained and/or otherwise configured to, without limitation: provide durable goods recommendations and/or custom manufacturing; provide medical diagnoses outside of the skincare field; provide cosmetic recommendations; provide allergy and/or medical condition diagnoses; provide dietary recommendations; provide lifestyle change recommendations; and so on.

Accordingly, one may appreciate that although many embodiments are disclosed above, that the operations and steps presented with respect to methods and techniques described herein are meant as exemplary and accordingly are not exhaustive. One may further appreciate that alternate step order or fewer or additional operations may be required or desired for particular embodiments.

Although the disclosure above is described in terms of various exemplary embodiments and implementations, it should be understood that the various features, aspects, and functionality described in one or more of the individual embodiments are not limited in their applicability to the particular embodiment with which they are described, but instead can be applied, alone or in various combinations, to one or more of the some embodiments of the invention, whether or not such embodiments are described and whether or not such features are presented as being a part of a described embodiment. Thus, the breadth and scope of the present invention should not be limited by any of the above-described exemplary embodiments but is instead defined by the claims herein presented.

In addition, it is understood that organizations and/or entities responsible for the access, aggregation, validation, analysis, disclosure, transfer, storage, or other use of private data including health data or health-related data such as described herein will preferably comply with published and industry-established privacy, data, and network security policies and practices. For example, it is understood that data and/or information obtained from remote or local data sources, only on informed consent of the subject of that data and/or information, should be accessed and aggregated only for legitimate, agreed-upon, and reasonable uses.

We claim:
1. A host server comprising:
a memory storing executable instructions; and
a processor configured to load the executable instructions from the memory to instantiate a service to communi- cably couple to a client application instantiated by a client device operated by a user, the service configured to:

receive from the client device, a user dataset comprising an input provided by the user to the client device, the input comprising demographic information about the user;

generate a query based on the demographic information to a database service storing location-specific information;

cause the query to be executed;

receive, a result from the database service, the result comprising historical geographic information about the local area of the user, the historical geographic information comprising water hardness information, seasonal temperature information, and at least one of:
  local area pollution information;
  local area humidity information; and
  local area seasonal ultraviolet light exposure information;

for each respective skin concern identifier of a set of skin concern identifiers stored in the memory:
  query the database service to retrieve a set of diagnostics comprising data signaling a respective skin concern identified by the respective skin concern identifier, the skin concern being an aesthetic skin concern or a medical skin concern;
  determine, for each respective diagnostic of the set of diagnostics, a credibility metric representing a first statistical likelihood based on the user dataset that the user exhibits the respective diagnostic; and
  determine, based on each credibility metric, a confidence metric representing a second statistical likelihood that the user does exhibit the respective skin concern;

ingest by a predictive model service comprising a trained predictive model, the user dataset, each respective confidence metric, and the historical geographic information, the trained predictive model trained against a dataset derived from customer review sentiment data correlating review author demographics and geographies against known ingredients of products reviewed by those review authors;

receive from the predictive model service, a diagnosis comprising a set of co-occurring skin concerns statistically likely to be exhibited by the user;

for each respective skin concern of the set of co-occurring skin concerns, query the database service to retrieve:
  a respective first list of ingredients that each exhibit a therapeutic effect for users exhibiting the respective skin concern; and
  a respective second list of ingredients that each exacerbate the respective skin concern;

generate a formulation for a custom skincare product by selecting a base from a set of skincare bases and at least one additive from a set of skincare base additives, at least one of the selected based and the one or more selected additives containing the first list of ingredients and none of the respective second list of ingredients;

causing a custom product to be manufactured by combining the selected skincare base and the selected one or more additives;

providing the custom product to the end user; and communicating a regimen recommendation in respect of the custom product to the client device to cause the client device to display the regimen recommendation to the user.

2. The host server of claim 1, wherein the user dataset comprises:
  a first data item comprising the input provided by the user to the client device;
  a second data item comprising a geographic location of the user; and
  a third data item comprising a demographic of the user.

3. The host server of claim 2, wherein the input comprises a set of answers provided by the user in response to the client device displaying at a display of the client device a set of diagnostic questions.

4. The host server of claim 2, wherein the regimen recommendation is based on the third data item of the user dataset.

5. The host server of claim 2, where in the service is further configured to:
  query the database service to retrieve a regimen modification based on the second data item of the user dataset and at least one or more of:
    a local area pollution metric;
    a local area humidity metric;
    a local area water hardness metric;
    a local area seasonal temperature average; and
    a local area seasonal ultraviolet light exposure average; wherein
  the regimen recommendation is based, at least in part, on the regimen modification.

6. The host server of claim 1, where in the service is further configured to:
  query the database service to retrieve an active ingredient interaction dataset;
  ingest by the predictive model service, each list of active ingredients and the active ingredient interaction dataset; and
  receive from the predictive model service, the regimen recommendation comprising a set of non-interacting active ingredients.

7. The host server of claim 1, wherein the custom product has a product type selected from:
  a facial cleanser;
  a topical sunscreen;
  a topical serum;
  an exfoliator;
  a moisturizer;
  a chemical peel;
  a toner;
  an eye cream; and
  a night cream.

8. The host server of claim 1, wherein at least one diagnostic of the set of diagnostics comprises:
  an age of the user;
  a gender of the user;
  a pregnancy condition of the user;
  a postpartum condition of the user;
  a menopause condition of the user;
  a medical condition of the user; or
  an ethnicity of the user.

9. The host server of claim 1, wherein:
  the user dataset comprises a demographic of the user; and
  determining the credibility metric for each respective diagnostic of the set of diagnostics comprises:
    ingesting by the predictive model service the respective diagnostic and the user dataset;

receiving from the predictive model service, a statistical likelihood that a person of the demographic exhibits the respective diagnostic; and determining the credibility metric based, at least in part, on the statistical likelihood output by the predictive model service.

10. The host server of claim 1, wherein:

the trained model is trained from one or more of data sources stored by or accessible to the database service of the host server; and the one or more data sources comprises one or more of:
skincare product review data; and
scientific reporting data.

11. The host server of claim 1, wherein the regimen recommendation comprises a suggestion to the user to use a skincare product containing a threshold number of active ingredients based on each respective list of active ingredients.

* * * * *